United States Patent [19]

Brighty et al.

[11] Patent Number: 5,037,834
[45] Date of Patent: Aug. 6, 1991

[54] HETEROCYCYLIC-SUBSTITUTED QUINOLINE-CARBOXYLIC ACIDS

[75] Inventors: Katherine E. Brighty, Groton; John A. Lowe, III, Stonington; Paul R. McGuirk, Gales Ferry, all of Conn.

[73] Assignee: Pfizer Inc., New York, N.Y.

[21] Appl. No.: 435,496
[22] PCT Filed: Dec. 18, 1987
[86] PCT No.: PCT/US87/03412
§ 371 Date: Aug. 1, 1989
§ 102(e) Date: Aug. 1, 1989

[51] Int. Cl.[5] .................... A61K 31/47; C07D 471/02
[52] U.S. Cl. .................................. 514/292; 514/215;
514/248; 514/249; 514/258; 514/300; 514/301;
514/302; 514/303; 546/81; 546/113; 546/114;
546/115; 546/118; 546/122; 544/234; 544/236;
544/249; 544/350; 540/578
[58] Field of Search ...................... 514/312, 292, 300;
546/81, 113, 122

[56] References Cited

U.S. PATENT DOCUMENTS

| 4,146,719 | 3/1979 | Irikura | 544/363 |
|---|---|---|---|
| 4,382,892 | 5/1983 | Hayakawa et al. | 260/243.3 |
| 4,530,930 | 7/1985 | Uno et al. | 514/312 |
| 4,571,396 | 2/1986 | Hutt et al. | 514/249 |
| 4,636,506 | 1/1987 | Gilligan et al. | 514/256 |
| 4,665,079 | 5/1987 | Culberteon | 514/312 |

FOREIGN PATENT DOCUMENTS 59-204194 11/1984 Japan.

Primary Examiner—Mukund J. Shah
Assistant Examiner—Jyothsna Ulnkat
Attorney, Agent, or Firm—Peter C. Richardson; Paul H. Ginsburg

[57] ABSTRACT

1-Substituted-6-fluoro-7-heterocyclic-1,4-dihydroquino-1-(or dihydronaphthyridin)-4-one carboxylic acids have antibacterial properties. The 7-heterocyclic group is a bicyclic group, one of the rings of which is saturated and the other ring of which is unsaturated.

7 Claims, No Drawings

HETEROCYCYLIC-SUBSTITUTED QUINOLINE-CARBOXYLIC ACIDS

BACKGROUND OF THE INVENTION

This invention relates to 1-substituted-6-fluoro-7-heterocyclic-1,4-dihydroquinol-(or dihydronaphthyridin)-4-one carboxylic acids, prodrug derivatives thereof, pharmaceutically acceptable acid addition or base salts thereof, antibacterial compositions containing these compounds, and a method of using these compounds.

Several U.S. patents disclose 1-substituted-6-fluoro-(or 6,8-difluoro)-7-heterocyclic-1,4-dihydroquinol-4-one carboxylic acids having antibacterial activity. In U.S. Pat. No. 4,146,719 the 7-substituent is a cyclic amine such as piperazinyl or pyrrolidinyl, in U.S. Pat. No. 4,530,930 the 7-substituent is 1-imidazolyl, in U.S. Pat. No. 4,636,506 the 7-substituent is 6-quinolyl and in U.S. Pat. No. 4,382,892 the 7-substituent is a cyclic amine such as pyrrolidine or piperidine.

Saturated bicyclic substitution at the 7-position is disclosed in Japanese Patent Publication 59204194 disclosing 7-diazabicycloalkane substitution.

The compounds of the invention are 7-bicyclic substituted, and one of the rings of the bicyclic group is saturated whereas the other one is unsaturated.

SUMMARY OF THE INVENTION

The compounds of the invention are 1,4-dihydroquinol-4-one-3-carboxylic acids of the formula

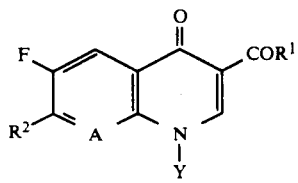

I or a pharmaceutically acceptable acid addition salt thereof, wherein

Y, when taken independently, is $(C_1-C_3)$alkyl, $(C_1-C_3)$hydroxyalkyl, vinyl, $(C_1-C_3)$haloalkyl wherein halo is fluoro or chloro, cyclopropyl, o,p-difluorophenyl, or p-fluorophenyl;

A, when taken independently, is C-H, C-F, C-Cl, C-OCH$_3$ or N;

or A is carbon and A and Y together form a group of the formula:

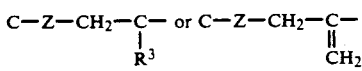

wherein Z is oxygen or CH$_2$, and R$^3$ is hydrogen, $(C_1-C_3)$alkyl, or halomethyl wherein halo is fluoro or chloro;

R$^1$ is hydroxy, $(C_1-C_6)$alkoxy, amino, $(C_1-C_6)$ alkylamino, or OM wherein M is a pharmaceutically acceptable cation; and R$^2$ is

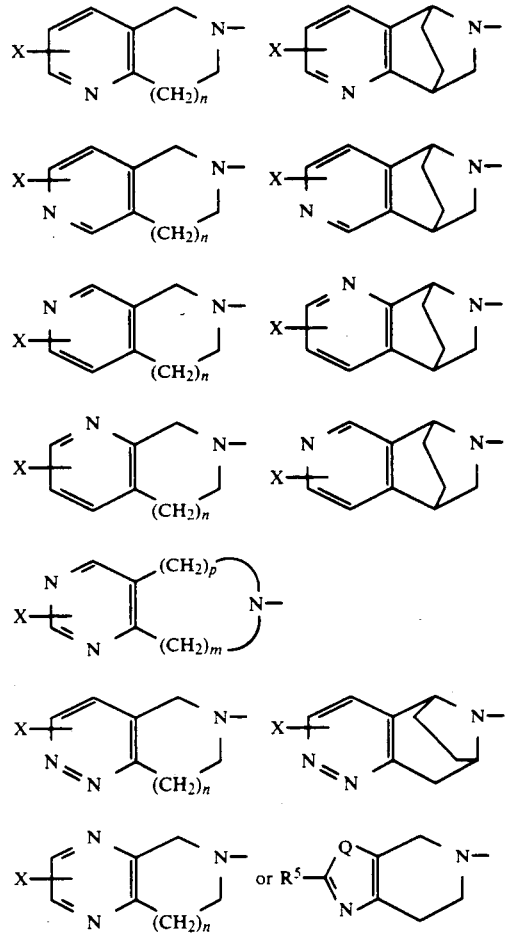

wherein

Q is O, S or NH, X is hydrogen, or one or two of CH$_2$NHR$^4$, NHR$^4$, or $(C_1-C_6)$alkylsulfonyl wherein R$^4$ is hydrogen or $(C_1-C_6)$alkyl, R$^5$ is hydrogen, $(C_1-C_5)$alkyl, hydroxy, amino, amino($C_1-C_4$)alkyl, di($C_1-C_4$)alkylamino, $(C_1-C_4)$alkylamino, $(C_1-C_4)$alkylamino-$(C_1-C_4)$alkyl, phenylamino, pyridylamino, or $(H_2N)_2C=N$, p is 1 and m is 1 or 2, or p is 2 and m is 1, and n is 0 or 1.

Preferred compounds of the invention are those wherein R$_1$ is hydroxy or OM wherein M is a pharmaceutically acceptable cation, those wherein Y is ethyl, vinyl, 2-fluoroethyl, cyclopropyl, p-fluorophenyl, or o,p-difluorophenyl, and those wherein A is C-H.

Specific preferred compounds of the invention are 7-[5-(2-amino-4,5,6,7-tetrahydrothiazolo[5,4-c]-pyridyl)]-1-ethyl-6-fluoro-1,4-dihydro-4-oxo-quinoline-3-carboxylic acid, 7-[5-(2-amino-4,5,6,7-tetrahydrothiazolo[5,4-c]pyridyl)]-1-cyclopropyl-6-fluoro-1,4-dihydro-4-oxo-quinoline-3-carboxylic acid, 1-cyclopropyl-6-fluoro-1,4-dihydro-7-[5-(2-methyl-4,5,6,7-tetrahydrothiazolo[5,4-c]pyridyl)]-4-oxo-quinoline-3-carboxylic acid, 1-cyclopropyl-6-fluoro-1,4-dihydro-4-oxo-7-[5-(2-(3-pyridyl)amino-4,5,6,7-tetrahydrothiazolo[5,4-c]pyridyl)]-quinoline-3-carboxylic acid, 1-ethyl-6-fluoro-1,4-dihydro-4-oxo-7-[6-(5,6,7,8-tetrahydro-1,6-naphthyridine)]-quinoline-3-carboxylic acid, 1-cyclopropyl-6-fluoro-1,4-dihydro-4-oxo-7-[6-(5,6,7,8-tetrahydro-1,6-naphthyridine)]-quinoline-3-carboxylic acid, 7-[6-(2-amino-5,6,7,8-tetrahydropyrido[4,3-d]-pyrimidyl)]-1- cyclopropyl-6-fluoro-1,4-dihydro-4-oxo-quinoline-3-carboxylic acid, 1-vinyl-6-fluoro-1,4-dihydro-4-oxo-7-[6-(5,6,7,8-tetrahydro-1,6-naphthyridine)]-quinoline-3-carboxylic acid, 1-cyclopropyl-6-fluoro-1,4-dihydro-4-oxo-7-[6-(5,6,7,8-tetrahydro-1,6-naphthyridine)]-1,8-naphthyridine-3-carboxylic acid, 9-fluoro-2,3-dihydro-3-methyl-7-oxo-10-[6-(5,6,7,8-tetrahydro-1,6-naphthyridine)]-7H-pyrido-[1,2,3-de]-1,4-benzoxazine-6-carboxylic acid, 6-fluoro-1-methylamino-1,4-dihydro-4-oxo-7-[6-(5,6,7,8-tetrahydro-1,6-naphthyridine)]-quinoline-3-carboxylic acid, 6-fluoro-1-(4-fluorophenyl)-1,4-dihydro-4-oxo-7-[6(5,6,7,8-tetrahydro-1,6-naphthyridine)]-quinoline-3-carboxylic acid, and 6-fluoro-1-(2-fluoroethyl)-1,4-dihydro-4-oxo-7-[6-(5,6,7,8-tetrahydro-1,6-naphthyridine)]-quinoline-3-carboxylic acid, or a pharmaceutically acceptable acid addition or base salt thereof.

The invention also relates to antibacterial compositions comprising an antibacterially effective amount of a compound of formula I and a pharmaceutically acceptable carrier. Preferred and specific preferred compositions are those wherein the compound of formula I is a preferred or a specific preferred compound as described above.

The invention further comprises a method of treating bacterial diseases or infections by administering to a subject affected by a bacterial disease an antibacterially effective amount of a compound of formula I. Preferred and specific preferred methods of treatment are those administering a preferred or specific preferred compound of formula I as described above.

DETAILED DESCRIPTION OF THE INVENTION

The term "halo" or "halogen" whenever used in the claims and the description means fluoro, chloro, bromo or iodo. The alkyl groups include both straight and branched carbon chains. The pyridyl group in the definition of $R_5$ may be 2-pyridyl, 3-pyridyl or 4-pyridyl, preferably 3-pyridyl.

The compounds of formula I may be prepared by reacting a compound of the formula

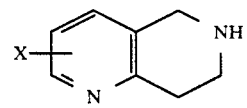

wherein $R^1$, Y and A are as defined above and L is a leaving group, with an amine of the formula $R^2H$ wherein $R^2$ is as defined above. Leaving group L may be halogen or alkylsulfonyl having one to three carbon atoms. Suitable leaving groups are for instance fluoro, chloro, methylsulfonyl or ethylsulfonyl. When $R^2$ contains an amino or alkylamino group, these groups may be protected to make them substantially inert under the reaction conditions. Suitable protecting groups are as follows: carboxylic acid groups such as formyl, acetyl or trifluoroacetyl; alkoxycarbonyl such as ethoxycarbonyl, t-butoxycarbonyl, $\beta,\beta,\beta$-trichloroethoxycarbonyl or $\beta$-iodoethoxycarbonyl; aryloxcarbonyl such as benzyloxycarbonyl, p-methoxybenzylcarbonyl or phenoxycarbonyl; silyl such as trimethylsilyl; trityl; tetrahydropyranyl; vinyloxycarbonyl; o-nitrophenylsulfenyl; diphenylphosphinyl; p-toluenesulfonyl, and benzyl.

After the reaction is completed, the protecting group is removed by methods known to those skilled in the art. For example, the ethoxycarbonyl group may be removed by acid or base hydrolysis and the trityl group may be removed by hydrogenolysis.

The above reaction between a compound of formula II and the amine $R^2H$ may be performed with or without a solvent, preferably at elevated temperature, for a sufficient time so that the reaction is substantially complete. Convenient solvents are solvents which are inert under the reaction conditions such as acetonitrile, tetrahydrofuran, ethanol, chloroform, dimethylsulfoxide, dimethylformamide, pyridine, picoline, and water. Mixtures of solvents may also be used. Reaction temperatures are conveniently in the range of from about 20° to about 150° C.

The reaction may be carried out in the presence of an acid acceptor such as an alkali metal or alkaline earth metal carbonate or bicarbonate, or a tertiary amine such as triethylamine, 1,8-diazabicyclo [5.4.0]-undec-7-ene, pyridine or picoline.

The starting compounds of formula II and $R^2H$ are known in the art or may be prepared by standard methods from known starting materials, as described below.

5,6,7,8-Tetrahydronaphthyridines 5,6,7,8-Tetrahydro-1,6-naphthyridines of the formula

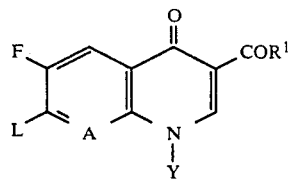

wherein X is hydrogen may be prepared by reacting 4-aminopyridine, and glycerol in a mixture of nitrobenzene and fuming sulfuric acid by the method of Paudler and Kress, J. Chem, Comm., 3 (1967). The formed 1,6-naphthyridine on reaction with benzylbromide forms a quaternary salt at position 6 which on reduction with sodium borohydride forms N-benzyltetrahydronaphthyridine. This intermediate on debenzylation with hydrogen and palladium-on-carbon catalyst results in the compound of formula 1 wherein X is hydrogen.

The compounds of formula 1, wherein X is $CH_2NHR^4$ at position 2, 3 or 4, may be prepared as described above for the compound wherein X is hydrogen. 1-Methylpropenal, 2-methylpropenal or methyl vinyl ketone are substituted for glycerol to give 2-, 3-, or 4-methyl-1,6-naphthyridine. On 6-benzylation, reduction and debenzylation, as above, the nitrogen in the 6 position of the tetrahydronaphthyridines formed may be protected by conversion to a carbamate group by reaction with an acid chloride such as tertiary butyl chloroformate or a benzoic acid derivative. Bromination of the methyl group with N-bromosuccinimide, substitution of the bromo by group $-NHR^4$ by reaction with an amide of the formula $CH_3C(O)NHR^4$ and sodium hydride in a polar solvent and acidification leads to a compound of the formula

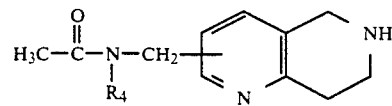

This compound is reacted with a compound of formula II above before deprotection of H₃CC(O)N(R₄)CH₂— to HN(R₄)CH₂— by hydrolysis with aqueous acid such as hydrogen chloride or acetic acid.

The compounds of formula 1 wherein X is 2-NHR⁴ or 2-($C_1$–$C_6$)alkylsulfonyl may be prepared from 5,6,7,8-tetrahydro-1,6-naphthyridine, protected at the 6-nitrogen as described above by oxidation with m-chloroperbenzoic acid (m-CPBA), then chlorination with phosphoroxy-chloride in xylene, and substitution of the 2-chlorine by reaction with R⁴NH₂ or ($C_1$–$C_6$)alkyl-sulfhydride. Oxidation with m-CPBA and deprotection as above results in the compound of formula 1 wherein X is 2-($C_1$–$C_6$)alkylsulfonyl. Protection of the R⁴NH— as an amide, as above, deprotection of the 6-nitrogen, coupling with the quinoline of formula II, and deprotection to X is 2-R⁴NH— results in a compound of formula I wherein R₂ is derived from formula 1 wherein X is 2-R⁴NH— and R⁴ is as defined before.

The compounds of formula 1 wherein X is 3-NHR⁴ or 3-($C_1$–$C_6$)alkylsulfonyl may be prepared from 6-nitrogen protected 5,6,7,8-tetrahydro-1,6-naphthyridine by bromination with bromine in acetic acid and substitution of the 3-bromine by reaction with R⁴NH₂ or ($C_1$–$C_6$)alkylsulfhydride. The subsequent procedure to obtain a compound of formula 1 wherein X is 3-($C_1$–$C_6$)alkylsulfonyl by oxidation and deprotection is as described above where X is 2-($C_1$–$C_6$)alkylsulfonyl. Similarly, the procedure to obtain compounds of formula I wherein R₂ is derived from formula 1 wherein X is 3-R⁴NH— and R⁴ is as defined above, is as described above for the corresponding compound wherein X is 2-R⁴NH—.

The compounds of formula 1 wherein X is 4-NHR⁴ or 4-($C_1$–$C_6$)alkylsulfonyl may be prepared from 6-nitrogen protected 5,6,7,8-tetrahydro-1,6-naphthyridine by oxidation with hydrogen peroxide or m-CPBA to the corresponding 1-oxide, methylation with dimethylsulfate to the 1-methoxy derivative, and reaction with R⁴NH₂ or ($C_1$–$C_6$)alkylsulfhydride for 4-substitution with loss of the 1-methoxy group. The subsequent steps are as described above with respect to 2-X and 3-X substitution.

5,6,7,8-Tetrahydro-1,7-naphthyridines 5,6,7,8-Tetrahydro-1,7-naphthyridines of the formula

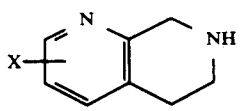

2 wherein X is hydrogen may be prepared analogously to the compound of formula 1 wherein X is hydrogen by reacting 2-hydroxy-3-aminopyridine and glycerol in a mixture of nitrobenzene and fuming sulfuric acid, removal of the 8-hydroxy by conversion to the 8-halo derivative followed by reduction, protection of the 7-nitrogen, reduction, and deprotection. The compounds of formula 2 wherein X is as defined before in connection with formula II, or a protected form thereof when X is NHR⁴ or CH₂NHR⁴, may be prepared as described above for corresponding 1,6-naphthyridines by starting from 2-hydroxy-3-aminopyridine instead of 4-aminopyridine.

5,6,7,8-Tetrahydro-2,6-naphthyridines 5,6,7,8-Tetrahydro-2,6-naphthyridines of the formula

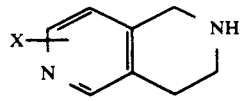

3 wherein X is as defined above in connection with formula I may be prepared by the reaction sequence shown in Scheme A. According to this procedure, N-benzyl-3-pyridone is reacted with pyrrolidine to form the enamine of formula III which undergoes cycloaddition with an appropriate X-substituted 1,2,4-triazine followed by elimination of nitrogen and pyrrolidine to give the fused pyridine of formula IV, Boger et al, J. Org. Chem., 46, 2179 (1981). The benzyl group is removed with hydrogen and palladium on carbon.

5,6,7,8-Tetrahydro-2,7-naphthyridines 5,6,7,8-Tetrahydro-2,7-naphthyridines of the formula

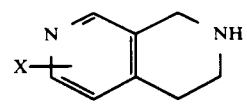

4

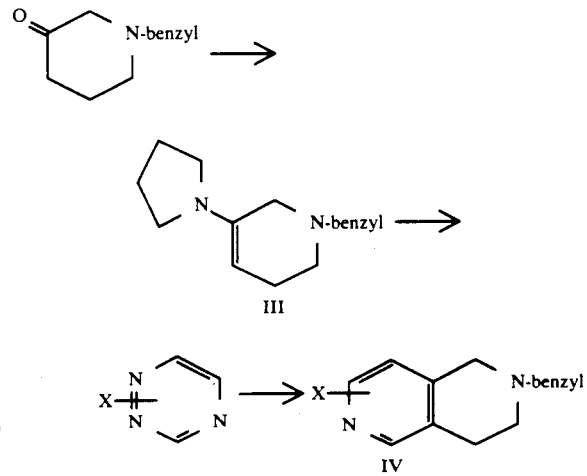

Scheme A

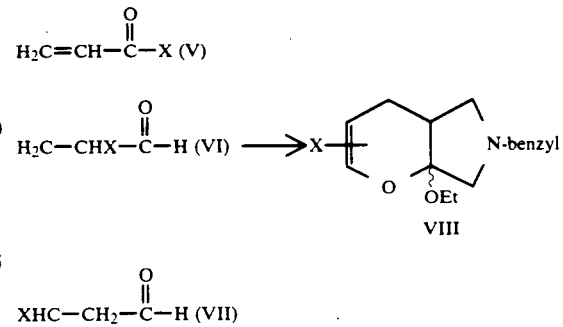

Scheme B wherein X is as defined above in connection with formula I may be prepared according to the method of Scheme A by using N-benzyl-4-pyridone instead of N-benzyl-3-pyridone.

2,6-Pyrrolidinopyridines 2,6-Pyrrolidinopyridines of the formula

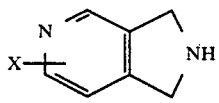

wherein X is as defined above with respect to formula I, may be prepared by the method of Scheme A by using N-benzyl-3-pyrrolidone instead of N-benzyl-3-pyridone.

1,6-Pyrrolidinopyridines 1,6-Pyrrolidinopyridines of the formula

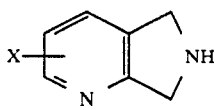

wherein X is as defined above with respect to formula I, provided that X is not 2-$NHR^4$ or 2-($C_1$-$C_6$)alkylsulfonyl, may be prepared as in Scheme B. Depending on whether X is 2-, 3-, or 4-substituted, a compound of formula V, VI, or VII, respectively, is reacted with the enol ether of N-benzyl-3-pyrrolidone to give the compound of formula VIII which is then reacted with ammonia and dehydrogenated with platinum on alumina to give compounds of formula 6, wherein X is as defined above, after debenzylation.

The compounds of formula 6 wherein X is 2-$NHR^4$ or 2-($C_1$-$C_6$)alkylsulfonyl may be prepared from the compound of formula 6 wherein X is hydrogen in the same manner as described above for the preparation of compounds of formula 1 wherein X is 2-$NHR^4$ or 2-($C_1$-$C_6$)alkylsulfonyl. Thus, the 6-nitrogen is suitably protected, and the 2-chloro compound formed on oxidation and chlorination is reacted with $R^4NH_2$ or ($C_1$-$C_6$)alkylsulfhydride. The compound wherein X is 2-($C_1$-$C_6$)alkylsulfonyl is then formed on oxidation and deprotection. The formed compound wherein X is 2-$NHR^4$ is not immediately 6-deprotected, but is first protected at the 2-nitrogen, then 6-deprotected and coupled, followed by deprotection at the 2-nitrogen.

5,8-Ethanotetrahydropyridopyridines 5,8-Ethanotetrahydropyrido [4,3-c] and [3,4-c]pyridines of the formulae

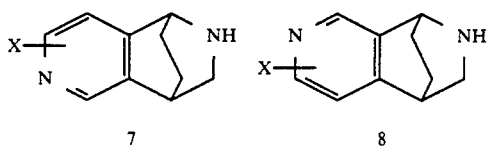

wherein X is as defined above with reference to formula I may be prepared from the bridged azabicyclic ketones of the formulae IX and X, respectively

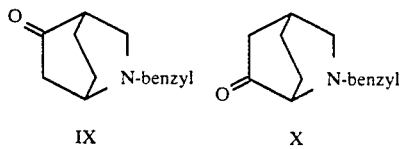

These ketones may be obtained from cyclohexadiene and benzyliminium ion by the method of Grieco et al, J. Am. Chem. Soc., 107, 1768 (1985), or from cyclohexadiene and methylenebisurethane with boron trifluoride etherate in benzene, and subsequent hydroboration and oxidation.

The formed ketones of formulae IX and X are separated by column chromatography such as silica gel chromatography, and reacted with pyrrolidone to form an enamine which on reaction with the appropriately substituted triazine forms N-benzyl substituted compounds of formulae 7 and 8, in accordance with the above described Scheme A. The oxidation state of sulfur is adjusted with peracid to form compounds wherein X is ($C_1$-$C_6$)alkylsulfonyl, and the nitrogen atom of compounds wherein X is $NHR^4$ is protected, and after coupling deprotected, as described above.

5,8-Ethano-5,6,7,8-tetrahydropyrido[4,3-b] and [3,4-b]pyridines of the formulae

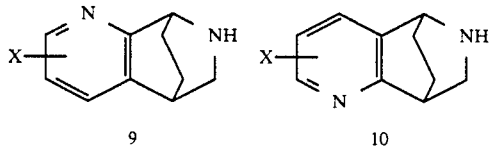

wherein X is as defined above with respect to formula I, except that X is not 2-$NHR^4$ or 2-($C_1$-$C_6$)alkylsulfonyl, may be prepared by reacting the compounds of formulae IX and X, respectively, with lithium diisopropylamide and subsequently with Meerwein's salt to give vinyl ethers of the formulae

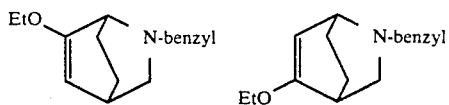

wherein Et is ethyl. The vinyl ethers are reacted with a compound of formula V, VI or VII to form cycloadducts in accordance with the reaction in Scheme B. After reaction with ammonia, dehydrogenation with platinum on alumina, and debenzylation with hydrogen, the compounds of formulae 9 and 10 are formed.

The compounds of formulae 9 and 10 wherein X is 2-$NHR^4$ or 2-($C_1$-$C_6$)alkylsulfonyl may be prepared from the compounds of formulae 9 and 10 wherein X is hydrogen in the same manner as described above for the preparation of compounds of formulae 1 and 6 wherein X is 2-$NHR^4$ or 2-($C_1$-$C_6$)alkylsulfonyl.

5,6,7,8-Tetrahydropyrido[4,3-c]pyridazine 5,6,7,8-Tetrahydropyrido[4,3-c]pyridazines of formulae wherein X is as defined above with respect to formula I may be prepared by the method of Salzmann et al, Arzneim. Forsch., 29, 1835 (1979).

4,5,6,7-Tetrahydrothiazolo[5,4-c]pyridines 4,5,6,7-Tetrahydrothiazolo[5,4-c]pyridines of the formula wherein $R^5$ is as defined above with respect to formula I may be prepared by the following methods.

The compounds of formula 13 wherein $R^5$ is amino, di($C_1$-$C_4$)alkylamino, ($C_1$-$C_4$)alkylamino, phenylamino, pyridylamino or $(H_2N)_2C=N$ may be prepared from methylvinyl ketone and phthalimide, and bromination of the formed product resulting in 1-bromo-4-phthalyl-2-butanone. This ketone is reacted with a thiourea of formula $R_5C(S)NH_2$ wherein $R_5$ is as defined above to form a thiazole of the formula wherein Phth is phthalyl. The thiazole XI is deprotected and cyclized with formaldehyde to form the desired thiazolopyridine.

The compounds of formula 13 wherein $R^5$ is hydrogen, ($C_1$-$C_4$)alkyl, amino($C_1$-$C_4$)alkyl, or ($C_1$-$C_4$)alkylamino($C_1$-$C_4$)alkyl may be prepared by reacting the appropriate thioamide of formula $R_5C(S)NH_2$ wherein $R_5$ is as just defined above with a cyclic α-bromo ketone of the formula wherein $R^6$ is a nitrogen-protecting group such as acetyl. On deprotection, the desired thiazolopyridine is formed. When $R^5$ is amino($C_1$-$C_4$)alkyl or ($C_1$-$C_4$)alkylamino($C_1$-$C_4$)alkyl, the amino may advantageously be protected with an acyl group during the cyclization to form the thiazole ring. The acyl group may be removed under acidic or basic conditions.

The compound of formula 13 wherein $R^5$ is hydroxy may be prepared by cyclization of N-acetyl-3-thiocyanate-4-piperidone under acid conditions.

4,5,6,7-Tetrahydrooxazolo[5,4-c]pyridines 4,5,6,7-Tetrahydrooxazolo[5,4-c]pyridines of the formula wherein $R_5$ is as defined above with respect to formula I may be prepared by the following methods.

The compounds of formula 14 wherein $R^5$ is amino, ($C_1$-$C_4$)alkylamino, phenylamino, pyridylamino, or $(H_2N)_2C=N$ may be prepared by reacting a substituted cyanamide of the formula $R^7NHCN$ wherein $R^7$ is hydrogen, ($C_1$-$C_4$)alkyl, phenyl, pyridyl or $(H_2N)_2C=N$, with an α-hydroxy ketone of the formula wherein $R^6$ is as defined above. The oxazolopyridine of formula 14 is formed on deprotection of the piperidine nitrogen.

The compound of formula 14 wherein $R^5$ is di($C_1$-$C_4$)alkylamino may be prepared by reacting the α-bromo ketone of formula XII with a dialkylurea of the formula $H_2NC(O)N(C_1$-$C_4)_2$, and subsequent hydrolysis.

The compounds of formula 14 wherein $R^5$ is ($C_1$-$C_4$)alkyl, amino($C_1$-$C_4$)alkyl or ($C_1$-$C_4$)alkylamino($C_1$-$C_4$)alkyl may be prepared by cyclization of a compound of the formula wherein $R^5$ is as defined immediately above, and $R^6$ is as defined before, with phosphous oxychloride. When $R^5$ is aminoalkyl or alkylaminoalkyl, the amino group may be advantageously protected during cyclization by an acyl or phthalimido group. The protecting group may be removed by treatment with hydrazine or by hydrolysis under acidic or basic conditions.

The compound of formula 14 wherein $R^5$ is hydrogen may be prepared by reacting the compound of formula XIII with formamide under acidic conditions.

The compound of formula 14 wherein $R^5$ is hydroxy may be obtained by reacting the α-bromo ketone of the formula wherein $R^6$ is as defined above, with potassium isocyanate and subsequent removal of $R^6$.

Tetrahydropyridopyrimidines and dihydropyrrolopyrimidines 5,6,7,8-Tetrahydropyrido[4,3-d] and [3,4-d]pyrimidines, and 6,7-dihydro-5H-pyrrolo[3,4-d]pyrimidines of the formula

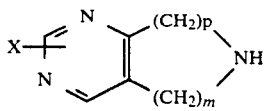

wherein X, m and p are as defined above with reference to formula I, may be prepared by the following methods.

Fused pyrimidines of formula 15, wherein X is hydrogen, 2-$CH_2NHR^4$ or 2-$NHR^4$, $R^4$ is as defined with reference to formula I, p is 2 and m is 1, may be formed from 4-piperidone wherein the nitrogen is protected by a nitrogen-protecting group such as acetyl. Thus, the N-protected 4-piperidone is reacted with $CH_3OCH[N(CH_3)_2]_2$ and the formed enamine is reacted with an amidine of the formula $XC(NH)NH_2$ wherein X is as defined immediately above in this paragraph.

The fused pyrimidines of formula 15 wherein X is 2-$(C_1-C_6)$alkylsulfonyl, p is 2 and m is 1 may be prepared from the piperidone of formula

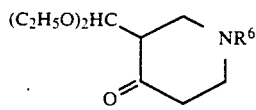

wherein $R^6$ is a nitrogen protecting group, by reaction with S-$(C_1-C_6)$alkylisothiourea, and oxidation with m-chloroperbenzoic acid followed by removal of $R^6$.

The fused pyrimidines of formula 15 wherein X is in the 4-position may be prepared from the piperidone of the formula

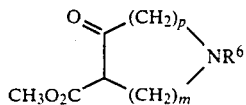

wherein $R^6$ is a nitrogen protecting group, by reaction with S-methylisothiourea, followed by treatment with aqueous acetic acid, and then with phosphorus oxychloride to provide an intermediate dichloropyrimidine of the formula

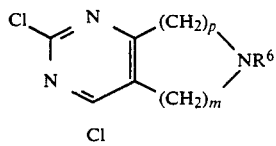

Nucleophilic substitution by reaction of the intermediate of formula XVIII with an amine $H_2NR^4$ wherein $R^4$ is as defined with reference to formula I, or a thiol $HS(C_1-C_6)$alkyl leads to 4-substitution. Hydrogenolysis of the 2-chloro, followed by oxidation in the case of the thiol substitution, and removal of $R^6$ results in compounds of formula 15 wherein X is 4-$NHR^4$ or 4-$(C_1-C_6)$alkylsulfonyl, and p and m are as defined with reference to formula I. Alternatively, to obtain disubstituted pyrimidines, the 2-chloro may be reacted with a second molecule of an amine or thiol as defined above, followed by oxidation of the formed sulfides to sulfones, and removal of $R^6$.

The fused pyrimidines may alternatively be prepared by a method of broader application than the above one by reacting a piperidone of the formula

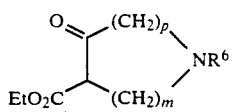

with an amidine of formula $$R^7C(NH)NH_2 \qquad XX$$

wherein $R^7$ is hydrogen, $CH_2NHR^4$, $NHR^4$, or $S(C_1-C_6)$alkyl and $R^4$ is hydrogen or $(C_1-C_6)$alkyl, to form an intermediate of the formula

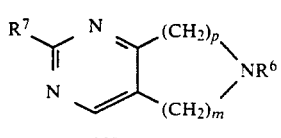

wherein $R^6$ and $R^7$ are as defined above. The 4-hydroxy group may be removed by conversion to the corresponding 4-chloride, and subsequent reduction as described above for removal of 2-chloro. The 4-chloro compound alternatively may be reacted with an amine or thiol to obtain disubstituted pyrimidines, after sulfur oxidation and $R^6$ removal as described before.

The following method allows for preparation of disubstituted compounds of formula 15 wherein the 4-substituent is $CH_2NHR^4$. An aminoester of the formula $R^4R^6NCH_2C(O)O(C_1-C_6)$alkyl is reacted with the enolate of N-protected 3-pyrrolidone or N-protected 3-piperidone or N-protected 4-piperidone to form a beta-diketone of the formula

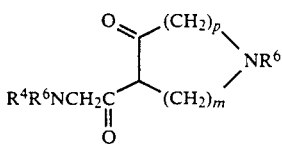

wherein $R^4$ is hydrogen or $(C_1-C_6)$alkyl and $R^6$ is a nitrogen protecting group. The diketone is reacted with an amidine of formula XX as defined above to form an intermediate of the formula

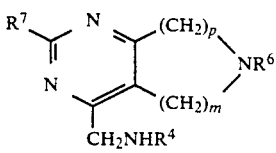

wherein $R^4$ is hydrogen or $(C_1-C_6)$alkyl and $R^7$ is as defined above. After sulfur oxidation when $R^7$ is $S(C_1-C_6)$alkyl and removal of $R^6$, compounds of formula 15 are formed wherein X is two of $CH_2NHR^4$, or 4-$CH_2NHR^4$ and one of hydrogen, $NHR^4$ or $(C_1-C_6)$alkylsulfonyl at the 2-position.

Tetrahydropyrido[3,4-b]pyrazines and dihydropyrrolo[3,4-b]pyrazines 5,6,7,8-Tetrahydropyrido[3,4-b]pyrazines and 6,7-dihydro-5H-pyrrolo[3,4-b]pyrazines of the formula

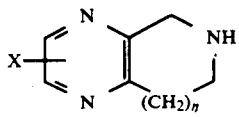

wherein X and n are as defined with reference to formula I may be prepared by the following methods.

In general, pyrazines may be prepared from reaction of alpha-diamines with alphadiketones.

The monosubstituted compounds of formula 16 wherein X is $NHR^4$ or $(C_1-C_6)$alkylsulfonyl may be prepared from reaction of alpha-aminoacetamide with N-protected 3,4-dioxopyrrolidone, or N-protected 3,4-dioxopiperidine, which may be obtained by sequential m-CPBA and Swern oxidation of the trimethylsilyl enol ether of N-protected 4-piperidone, to obtain a mixture of monoketones of the formula

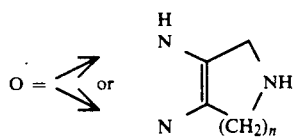

wherein n is 1 or 2. Chlorination and nucleophilic substitution by reaction with an amine $H_2NR^4$, wherein $R^4$ is hydrogen or $(C_1-C_6)$alkyl, or a thiol $HS(C_1-C_6)$alkyl leads to a mixture of compounds of formula 16 wherein X is one of $NHR^4$ or $(C_1-C_6)$alkylsulfonyl after oxidation of the thioethers and removal of the N-protecting group. The X-substituent may be at either of the two positions in the pyrazine ring. The mixture may be separated by column chromatography.

The compounds of formula 16 wherein X is hydrogen or $CH_2NHR^4$ may be prepared by cyclocondensation of N-protected 3,4-dioxopyrrolidone or N-protected 3,4-dioxopiperidine with a diamine $H_2NCH_2CHXNH_2$ wherein X is hydrogen or $CH_2NR^4R^6$, followed by dehydrogenation with $KOH/MnO_2$ or $KOH/CuO$ and removal of the N-protecting groups. A mixture of mono-$CH_2NHR^4$-substituted compounds is obtained. Separation of the positional isomers is by standard column chromatography on silica gel.

The disubstituted pyrazines of formula 16 may be obtained as described above from the above-mentioned N-protected dioxopyrrolidone or piperidone by reaction with alpha-$CH_2NR^4R^6$-alpha-aminoacetamide rather than alpha-aminoacetamide, followed by chlorination and nucleophilic substitution, oxidation of the thioether, and removal of the nitrogen-protecting group or groups.

The pharmaceutically acceptable base salts of the compounds of formula I are formed with metals or amines. Examples of suitable metals used as cations are alkali metals such as sodium or potassium and alkaline earth metals such as magnesium and calcium. Suitable amines are for example N,N-dibenzylethylenediamine, chloroprocaine, choline, diethanolamine, ethylenediamine, N-methylglucamine, and procaine.

The pharmaceutically acceptable acid addition salts of compounds (I) are prepared in a conventional manner by treating a solution or suspension of the free base (I) with about one chemical equivalent of a pharmaceutically acceptable organic or inorganic acid. Suitable acids are hydrochloric, sulfuric, phosphoric, acetic, citric, oxalic, malonic, salicylic, malic, lactic, p-toluenesulfonic, gluconic, fumaric, succinic, ascorbic, maleic, and methanesulfonic acid. The acid addition salts may be advantageous because of certain physical properties such as solubility in polar solvents, particularly water.

The compounds of formula I may exist in unsolvated or solvated form including hydrated forms. In general, the state of solvation does not affect the anti-bacterial properties of the compounds (I).

The compounds of formula I and the pharmaceutically acceptable acid addition and base salts thereof are useful in the treatment of bacterial infections of broad spectrum.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5-5000 ppm, preferably 25-500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1-50 mg/kg/day, advantageously 0.2-10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 50 mg/kg/day, advantageously 0.5-5 mg/kg/day given in a single dose or up to 3 divided doses. For intramuscular or intravenous administration, dosage levels are about 0.1-20 mg/kg/day, advantageously 0.5-5 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the preparation of the compounds of the invention. The temperatures are in degrees Celsius.

EXAMPLE 1

7-[5-(2-Amino-4,5,6,7-tetrahydrothiazolo[5,4-c]pyridyl)]-1-cyclopropyl-6-fluoro-1,4-dihydro-4-oxo-quinoline-3-carboxylic acid

A. A solution of 2-amino-4,5,6,7-tetrahydrothiazolo-[5,4-c]pyridine (0.75 g, 4.83 mmol) in dimethylsulfoxide (75 ml) was treated with 1-cyclopropyl-6,7-difluoro-1,4-dihydro-4-oxo-quinoline-3-carboxylic acid (1.28 g, 4.83 mmol) and heated to 80° overnight. The dimethylsulfoxide was then removed by distillation, and the residue was triturated with isopropanol, filtered, washed with ether and dried under nitrogen to provide the title product as a yellow solid, m.p. 245°–250° (decomp.) (1.81 g, 4.52 mmol, 94% yield).

$^1$H NMR (DMSO-$d_6$): 8.57 (s, 1H), 7.86 (d, J=13 Hz, 1H), 7.54 (d, J=8 Hz, 1H), 6.82 (bs, 2H), 4.40 (bs, 2H), 3.76 (m, 1H), 3.70 (m, 2H), 2.62 (bs, 2H), 1.30 (bd, J=6 Hz, 2H), 1.13 (bs, 2H).

Sodium 7-[5-(2-amino-4,5,6,7-tetrahydrothiazolo[5,4-c]-pyridyl)]-1-cyclopropyl-6-fluoro-1,4-dihydro-4-oxo-quinoline-3-carboxylate

B. 7-(2-Amino-4,5,6,7-tetrahydrothiazolo[5,4-c]pyridyl)-1-cyclopropyl-6-fluoro-1,4-dihydro-4-oxo-quinoline-3-carboxylic acid (1.60 g, 4.00 mmol) was suspended in water (150 ml) and treated with sodium hydroxide (4.0 ml of a 1N solution, 4.0 mmol). The reaction mixture was stirred vigorously for 0.5 hour, and the resulting solution was filtered and freeze dried. The title product was obtained as a yellow solid, m.p. 230°–250° (decomp.) (1.496 g, 3.54 mmol, 89% yield).

$^1$H NMR (D$_2$O): 8.40 (s, 1H), 7.85 (d, J=13 Hz, 1H), 7.54 (d, J=7 Hz, 1H), 4.32 (bs, 2H), 3.64 (bs, 2H), 3.49 (bs, 1H), 2.51 (bs, 2H), 1.18 (bd, J=7 Hz, 2H), 0.96 (bs, 2H).

EXAMPLE 2

7-[5-(2-Amino-4,5,6,7-tetrahydrothiazolo[5,4-c]pyridyl)]-1-ethyl-6-fluoro-1,4-dihydro-4-oxo-quinoline-3-carboxylic acid

A solution of 2-amino-4,5,6,7-tetrahydrothiazolo-[5,4-c]pyridine (50 mg, 0.322 mmol) in dimethylsulfoxide (10 ml) was treated with 1-ethyl-6,7-difluoro-1,4-dihydro-4-oxo-quinoline-3-carboxylic acid (83 mg, 0.327 mmol) and heated to 80° for 18 hours. The dimethylsulfoxide was removed by distillation. The residue was triturated with n-butanol, filtered, washed with n-butanol and ether, and dried in vacuo. Tritration with n-propanol provided the title product as a yellow solid, m.p. 235°–240° (decomp.) (95 mg, 0.24 mmol, 74% yield).

$^1$NMR (DMSO-$d_6$): 8.91 (s, 1H), 7.92 (d, J=13 Hz, 1H), 7.17 (d, J=8 Hz, 1H), 6.84 (bs, 2H), 4.56 (bq, 2H), 4.40 (bs, 2H), 3.67 (m, 2H) 2.62 (bs, 2H), 1.36 (t, J=7 Hz, 3H).

EXAMPLE 3

7-[5-(2-Amino-4,5,6,7-tetrahydrothiazolo[5,4-c]pyridyl)]-1-cyclopropyl-6,8-difluoro-1,4-dihydro-4-oxo-quinoline-3-carboxylic acid

A mixture of 2-amino-4,5,6,7-tetrahydrothiazolo-[5,4-c]pyridine (54.2 mg, 0.349 mmol) and 1-cyclopropyl-6,7,8-trifluoro-1,4-dihydro-4-oxo-quinoline-3-carboxylic acid (90.0 mg, 0.318 mmol) in dimethylsulfoxide (4 ml) was heated to 80° C. for 18 hours. The solvent was removed in vacuo and the residue triturated with isopropanol to yield the title product as a yellow solid, m.p. 228° (81.9 mg, 0.20 mmol, 63% yield).

EXAMPLE 4

7-[5-(2-Amino-4,5,6,7-tetrahydrothiazolo[5,4-c]pyridyl)]-6-fluoro-1-(4-fluorophenyl)-1,4-dihydro-4-oxo-quinoline-3-carboxylic acid

A solution of 2-amino-4,5,6,7-tetrahydrothiazolo-[5,4-c]pyridine (53.5 mg, 0.344 mmol) and 6,7-difluoro-1-(4-fluorophenyl)-1,4-dihydro-4-oxo-quinoline-3-carboxylic acid (100 mg, 0.313 mmol) in dimethylsulfoxide (6 ml) was heated to 80° for 96 hours. The solvent was removed in vacuo, and the residue triturated with isopropanol and isopropyl ether. The resulting solid was subjected to column chromatography (eluant: 79:20:1 chloroform: methanol: concentrated aqueous ammonium hydroxide) to provide the title product as a yellow solid, m.p. 236°–237° (53.1 mg, 0.12 mmol, 39% yield).

EXAMPLE 5

10-[5-(2-Amino-4,5,6,7-tetrahydrothiazolo[5,4-c]pyridyl)]-9-fluoro-2,3-dihydro-3-methyl-7-oxo-7H-pyrido[1,2,3-de]-1,4-benzoxazine-6-carboxylic acid

A mixture of 2-amino-4,5,6,7-tetrahydrothiazolo-[5,4-c]pyridine (133.3 mg, 0.858 mmol) and 9,10-difluoro-2,3-dihydro-3-methyl-7-oxo-7H-pyrido[1,2,3-de-]-1,4-benzoxazine-6-carboxylic acid (219.4 mg, 0.78 mmol) in dimethylsulfoxide (10 ml) was heated to 80° for 48 hours. The reaction mixture was treated with triethylamine (0.109 ml, 0.78 mmol) and allowed to react at 80° for an additional 18 hours. After a second treatment with triethylamine (0.109 ml, 0.78 mmol) and an additional 72 hours of reaction at 80°, the solvent was removed in vacuo, and the residue washed repeatedly with isopropanol. Silica gel chromatography (eluant: 79:20:1 chloroform: methanol: concentrated aqueous ammonium hydroxide) provided the title product as a solid, m.p. 228° (decomp.).

$^1$H NMR (DMSO-$d_6$): 8.96 (s, 1H), 7.61 (d, J=13 Hz, 1H), 6.80 (m, 2H), 4.92 (m, 1H), 4.6 (bd, J=10 Hz, 1H), 4.39 (bd, J=10 Hz, 1H), 4.33 (bs, 1H), 3.55 (m, 2H), 2.63 (bs, 2H) 1.47 (d, J=7 Hz, 3H).

EXAMPLE 6

1-Cyclopropyl-6-fluoro-1,4-dihydro-4-oxo-7-[5-(2-(3-pyridyl)amino-4,5,6,7-tetrahydrothiazolo[5,4-c]pyridyl)]-quinoline-3-carboxylic acid

A solution of 2-(3-pyridyl)amino-4,5,6,7-tetrahydrothiazolo[5,4-c]pyridine (0.270 g, 1.16 mmol) and triethylamine (0.162 ml, 1.16 mmol) in dimethylsulfoxide (12 ml) was treated with 1-cyclopropyl-6,7-difluoro-1,4-diydro-4-oxo-quinoline-3-carboxylic acid (0.307 g, 1.16 mmol) and heated to 80° for 24 hours. The reaction mixture was filtered, and the filtrate was concentrated in vacuo to provide the title product as pale white solid, m.p. 160° (decomp.) (0.305 g, 0.64 mmol, 55% yield).

$^1$H NMR (DMSO-$d_6$): 8.65 (d, J=3 Hz, 1H), 8.56 (s, 1H), 8.07 (m, 2H), 7.85 (d, J=13 Hz, 1H), 7.55 (d, J=7 Hz, 1H), 7.24 (dd, J=8, 5 Hz, 1H), 4.51 (bs, 2H), 3.74 (m, 3H), 2.77 (vbs, 2H), 1.27 (bd, J=6 Hz, 2H), 1.11 (bs, 2H).

EXAMPLE 7

7-[5-(2-Phenylamino-4,5,6,7-tetrahydrothiazolo[5,4-c]-pyridyl)]-1-cyclopropyl-6-fluoro-1,4-dihydro-4-oxo-quinoline-3-carboxylic acid A solution of 2-phenylamino-4,5,6,7-tetrahydrothiazolo[5,4-c]pyridine (0.281 g, 1.21 mmol) in dimethylsulfoxide (15 ml) was treated with 1-cyclopropyl-6,7-difluoro-1,4-dihydro-4-oxo-quinoline-3-carboxylic acid (0.259 g, 0.979 mmol) and heated to 80° overnight. The dimethylsulfoxide was removed by distillation, and the residue was triturated with isopropanol, filtered, washed with ether and dried to provide the title product as a yellow powder, decomp. >200° (0.309 g, 0.65 mmol, 66% yield).

$^1$H NMR (DMSO-$d_6$): 8.62 (s, 1H), 7.93 (d, J=13 Hz, 1H), 7.60 (m, 3H), 7.28 (m, 2H), 6.91 (m, 1H), 4.56 (bs, 2H), 3.80 (bs, 3H), 2.81 (bs, 2H), 1.32 (bd, J=6 Hz, 2H), 1.17 (bs, 2H).

EXAMPLE 8

1-Cyclopropyl-6-fluoro-1,4-dihydro-7-[5-(2-dimethylamino-4,5,6,7-tetrahydrothiazolo [5,4-c]pyridyl)]-4-oxo-quinoline-3-carboxylic acid 2-Dimethylamino-4,5,6,7-tetrahydrothiazolo [5,4-c]-pyridine (128.5 mg, 0.702 mmol) was combined with triethylamine (0.10 ml, 0.7 mmol) in dimethylsulfoxide (15 ml) and treated with 1-cyclopropyl-6,7-difluoro-1,4-diihydro-4-oxo-quinoline-3-carboxylic acid (0.185 g, 0.702 mmol). The reaction mixture was heated to 80° for 48 hours, then cooled and concentrated in vacuo. The residue was triturated with isopropyl ether and with isopropanol to provide the title product as a brown solid, m.p. 190°–191° (decomp.) (286 mg, 0.67 mmol, 95% yield).

$^1$H NMR (DMSO-$d_6$): 8.60 (s, 1H), 7.88 (d, J=13 Hz, 1H), 7.56 (d, J=7 Hz, 1H), 4.49 (bs, 2H), 3.73 (m, 3H), 3.00 (s, 6H), 2.71 (bs, 2H), 1.31 (bd, J=6 Hz, 2H), 1.16 (bs, 2H).

EXAMPLE 9

1-Cyclopropyl-7-[5-(2-Ethylamino-4,5,6,7-tetrahydrothiazolo[5,4-c]pyridyl)]-6-fluoro-1,4-dihydro-4-oxo-quinoline-3-carboxylic acid A solution of 2-ethylamino-4,5,6,7-tetrahydrothiazolo [5,4-c]pyridine (0.100 g, 0.546 mmol) in dimethylsufoxide (8 ml) was treated with 1-cyclopropyl-6,7-difluoro-1,4-dihydro-4-oxo-quinoline-3-carboxylic acid (0.115 g, 0.436 mmol) and heated to 80° overnight. A light yellow precipitate was removed by filtration, washed with isopropanol and ether and dried, providing the title product as a light yellow powder, m.p. 280°–287° (decomp.) (93.5 mg, 0.22 mmol, 50% yield).

$^1$H NMR (DMSO-$d_6$): 8.60 (s, 1H), 7.90 (d, J=13 Hz, 1H), 7.57 (d, J=8 Hz, 1H), 7.43 (t, J=5 Hz, 1H), 4.44 (bs, 2H), 3.77 (m, 3H), 3.20 (m, 2H), 2.67 (bs, 2H), 1.30 (bd, J=6 Hz, 2H), 1.13 (m, 5H).

EXAMPLE 10

1-Cyclopropyl-6-fluoro-7-[5-(2-guanidino-4,5,6,7-tetrahydrothiazolo[5,4-c]pyridyl)]-1,4-dihydro-4-oxo-quinoline-3-carboxylic acid 2-Guanidino-4,5,6,7-tetrahydrothiazolo[5,4-c]pyridine (111.7 mg, 0.566 mmol), 1-cyclopropyl-6,7-difluoro-1,4-dihydro-4-oxo-quinoline-3-carboxylic acid (149.5 mg, 0.566 mmol) and triethylamine (0.095 ml, 0.68 mmol) were combined in dimethylsulfoxide (10 ml) and heated to 80° for 24 hours. Removal of solvent in vacuo gave a solid which was washed thoroughly with isopropanol to provide the title product as a solid, m.p. 259°–270° (decomp.) (195 mg, 0.44 mmol, 78% yield).

$^1$H NMR (DMSO-$d_6$): 8.60 (s, 1H), 7.88 (d, J=13 Hz, 1H), 7.57 (d, J=7 Hz, 1H), 7.00 (bs, 4H), 4.49 (bs, 2H), 3.75 (m, 3H), 2.72 (bs, 2H), 1.29 (bd, J=6 Hz, 2H), 1.14 (bs, 2H).

EXAMPLE 11

1-Cyclopropyl-6-fluoro-1,4-dihydro-7-[5-(2-methyl-4,5,6,7-tetrahydrothiazolo[5,4-c]pyridyl)]-4-oxo-quinoline-3-carboxylic acid A solution of 2-methyl-4,5,6,7-tetrahydrothiazolo-[5,4-c]pyridine (0.243 g, 1.57 mmol) in dimethylsulfoxide (15 ml) was treated with 1-cyclopropyl-6,7-difluoro-1,4-dihydro-4-oxo-quinoline-3-carboxylic acid (0.412 g, 1.55 mmol) and triethylamine (0.22 ml, 1.6 mmol) and heated to 80° for 72 hours. The dimethylsulfoxide was then removed by distillation, and the residue was chromatographed on silica gel (eluant: 89:10:1 chloroform-:methanol:concentrated ammonium hydroxide) to provide the title product as a yellow solid, mp 253°–255° (250 mg, 0.63 mmol, 40% yield).

$^1$H NMR (DMSO-$d_6$): 8.62 (s, 1H), 7.93 (d, J=13 Hz, 1H), 7.60 (d, J=8 Hz, 1H), 4.67 (bs, 2H), 3.79 (m, 3H), 2.90 (m, 2H), 1.30 (bd, J=6 Hz, 2H), 1.16 (bs, 2H).

EXAMPLE 12

1-Ethyl-6-fluoro-1,4-dihydro-4-oxo-7-(6-[5,6,7,8-tetrahydro-1,6-naphthyridine]-quinoline-3-carboxylic acid A mixture of 5,6,7,8-tetrahydro-1,6-naphthyridine (600 mg, 4.48 mmol) and 1-ethyl-6,7-difluoro-1,4-dihydro-4-oxo-quinoline-3-carboxylic acid (506 mg, 2 mmol) in pyridine (5 ml) was heated to 95° for 3 hours. The reaction mixture was cooled and filtered; the precipitate was washed with a small quantity of cold chloroform, then washed extensively with ethyl ether. Upon drying, the title product was obtained as a solid, m.p. 235°–236° (333 mg, 0.9 mmol, 45% yield).

EXAMPLE 13

1-Cyclopropyl-6-fluoro-1,4-dihydro-7-[5-(2-hydroxy-4,5,6,7-tetrahydrothiazolo[5,4-c]pyridyl)]-4-oxo-quinoline-3-carboxylic acid 2-Hydroxy-4,5,6,7-tetrahydrothiazolo[5,4-c]-pyridine (101.8 mg, 0.65 mmol) and 1-cyclopropyl-6,7-difluoro-1,4-dihydro-4-oxo-quinoline-3-carboxylic acid (171.6 mg, 0.65 mmol) were combined in dimethylsulfoxide (10 ml) and heated to 80° for 48 hours. The mixture was then cooled and filtered, and the filtrate concentrated in vacuo to provide a yellow solid, which was washed with isopropyl ether, triturated with isopropanol and then washed repeatedly with methanol to provide the title product as a yellow solid, m.p. 231° (Decomp.) (70.5 mg, 0.18 mmol, 28% yield).

$^1$H NMR (DMSO-$d_6$): 8.65 (s, 1H), 7.94 (d, J=13 Hz, 1H) 7.60 (d, J=7 Hz, 1H), 4.30 (s, 2H), 3.82 (bs, 1H), 3.76 (m, 2H), 2.55 (m, 2H), 1.35 (d, J=6 Hz, 2H), 1.20 (bs, 2H).

EXAMPLE 14

7-[6-(2-Amino-5,6,7,8-tetrahydropyrido[4,3-d]pyrimidyl)]-1-cyclopropyl-6-fluoro-1,4-dihydro-4-oxo-quinoline-3-carboxylic acid 2-Amino-5,6,7,8-tetrahydropyrido[4,3-d]pyrimidine (24.3 mg, 0.161 mmol) and 1-cyclopropyl-6,7-difluoro-1,4-dihydro-4-oxo-quinoline-3-carboxylic acid (34 mg, 0.129 mmol) were combined in dimethylsulfoxide (3 ml) and heated to 80° for 16 hours. The resulting white precipitate was filtered and washed sequentially with isopropanol and ether to provide the title product as a white solid, m.p. 295°–305° (decomp.) (39.3 mg, 0.1 mmol, 62% yield).

$^1$H NMR (DMSO-$d_6$): 8.69 (s, 1H), 8.20 (s, 1H), 7.98 (d, J=13 Hz, 1H), 7.65 (d, J=7 Hz, 1H), 6.54 (s, 2H), 4.48 (s, 2H), 3.86 (m, 1H), 2.86 (m, 2H), 1.35 (bd, J=5 Hz, 2H), 1.20 (bs, 2H).

EXAMPLE 15

1-Cyclopropyl-6-fluoro-1,4-dihydro-4-oxo-7-(6-[5,6,7,8-tetrahydro-1,6-naphthyridine])-quinoline-3-carboxylic acid A mixture of 5,6,7,8-tetrahydro-1,6-naphthyridine (2.5 g, 18.6 mmol) and 1-cyclopropyl-6,7-difluoro-1,4-dihydro-4-oxo-quinoline-3-carboxylic acid (2.5 g, 9.4 mmol) in pyridine (25 ml) was heated to 85° for 3 hours. The reaction mixture was filtered, and the precipitate washed with chloroform. Recrystallization from dimethylformamide provided the title product as a solid, m.p. 273°–274° (1.9 g, 5.0 mmol, 53% yield).

EXAMPLE 16

1-Cyclopropyl-6-fluoro-1,4-dihydro-4-oxo-7-[6-(5,6,7,8-tetrahydro-1,6-naphthyridine)]-1,8-naphthyridine-3-carboxylic acid A mixture of 5,6,7,8-tetrahydro-1,6-naphthyridine (402 mg, 3 mmol) and 7-chloro-1-cyclopropyl-6-fluoro-1,4-dihydro-4-oxo-1,8-naphthyridine-3-carboxylic acid (282 mg, 1 mmol) in pyridine (5 ml) was heated to 80° for 5 hours. The reaction mixture was cooled and filtered; the precipitate was washed extensively with chloroform and ether. The filtrate was washed with water, dried over magnesium sulfate, and concentrated in vacuo to provide a solid residue. This was slurried with ether, filtered, and subjected to column chromatography (99:1 chloroform:methanol) to provide a slightly off-white solid. Recrystallization from acetonitrile yielded the title product, m.p. 264° (110 mg, 0.29 mmol, 29% yield).

EXAMPLE 17

9-Fluoro-2,3-dihydro-3-methyl-7-oxo-10-(6-[5,6,7,8-tetrahydro-1,6-naphthyridine])-7H-pyrido[1,2,3-de]-1,4-benzoxazine-6-carboxylic acid A mixture of 5,6,7,8-tetrahydro-1,6-naphthyridine (402 mg, 3 mmol) and 9,10-difluoro-2,3-dihydro-3-methyl-7-oxo-7H-pyrido[1,2,3-de]-1,4-benzoxazine-6-carboxylic acid (281 mg, 1 mmol) in dimethylsulfoxide (5 ml) was heated to 80° for 18 hours. The reaction mixture was poured into water, and the precipitate was separated by filtration; the filtrate was extracted twice with chloroform, and the combined organic layers were dried over magnesium sulfate. Removal of solvent in vacuo provided a residue which was combined with the precipitate and subjected to column chromatography (eluted with chloroform, then 99:1 chloroform:methanol). The material obtained in this way was subsequently recrystallized from a minimum quantity of chloroform to provide the title product, m.p. 254°–255° (21 mg, 0.05 mmol, 5% yield).

EXAMPLE 18

6-Fluoro-1,4-dihydro-1-methyl-4-oxo-7-(6-[5,6,7,8-tetrahydro-1,6-naphthyridine])-quinoline-3-carboxylic acid A solution of 5,6,7,8-tetrahydro-1,6-naphthyridine hydrochloride (295 mg, 1.75 mmol), 6,7-difluoro-1,4-dihydro-1-methyl-4-oxo-quinoline-3-carboxylic acid (239 mg, 1 mmol) and 1,8-diazabicyclo[5.4.0]undec-7-ene (533 mg, 3.5 mmol) in pyridine (5 ml) was heated to 80° for 1 hour; the reaction mixture was then cooled and filtered. The precipitate was washed with chloroform and ether, dried, and recrystallized once from isopropyl alcohol and once from dimethylsulfoxide to yield the title product, m.p. 305° (75 mg, 0.21 mmol, 21% yield).

EXAMPLE 19

6-Fluoro-1,4-dihydro-1-methylamino-4-oxo-7-(6-[5,6,7,8-tetrahydro-1,6-naphthyridine])-quinoline-3-carboxylic acid A solution of 5,6,7,8-tetrahydro-1,6-naphthyridine (268 mg, 2 mmol) and 6,7-difluoro-1,4-dihydro-1-methylamino-4-oxo-quinoline-3-carboxylic acid (254 mg, 1 mmol) in pyridine (3 ml was heated to 80° for 18 hours. the reaction mixture was cooled and filtered; the precipitate was washed well with chloroform and ether, then recrystallized from dimethylsulfoxide to provide the title product, m.p. 275° (280 mg, 0.76 mmol, 76% yield).

EXAMPLE 20

6-Fluoro-1-(4-fluorophenyl)-1,4-dihydro-4-oxo-7-(6-[5,6,7,8-tetrahydro-1,6-naphthyridine])-quinoline-3-carboxylic acid A solution of 5,6,7,8-tetrahydro-1,6-naphthyridine (268 mg, 2 mmol) and 6,7-difluoro-1-(4-fluorophenyl)-1,4-dihydro-4-oxo-quinoline-3-carboxylic acid (319 mg, 1 mmol) in pyridine (3 ml) was heated to 80° for 4 hours, and 60° for 16 hours. The reaction was filtered, and the precipitate was washed with chloroform. The filtrate was diluted with additional chloroform and washed with water, then with 1N hydrochloric acid; the combined aqueous washes were treated with sodium bicarbonate and back extracted with chloroform. The combined organic layers were dried over magnesium sulfate and concentrated in vacuo to yield an off-white solid. This material was combined with the precipitate and recrystallized from ethyl acetate to yield the title product, m.p. 254°–255° (110 mg, 0.25 mmol, 25% yield).

EXAMPLE 21

1-Ethyl-6,8-difluoro-1,4-dihydro-4-oxo-7-(6-[5,6,7,8-tetrahydro-1,6-naphthyridine])-quinoline-3-carboxylic acid A mixture of 5,6,7,8-tetrahydro-1,6-naphthyridine (300 mg, 2.24 mmol) and 1-ethyl-6,7,8-trifluoro-1,4-dihydro-4-oxo-quinoline-3-carboxylic acid (300 mg, 1.25 mmol) in pyridine (5 ml) was heated to 80° for 90 hours. The reaction mixture was diluted with chloroform (100 ml) and washed with water. The organic layer was concentrated in vacuo, and the solid residue was triturated with ethyl ether; the resulting residue was dissolved in chloroform (100 ml) and extracted with 1N hydrochloric acid. The aqueous layer was then brought to pH 7 with saturated aqueous sodium bicarbonate solution; the resulting precipitate was collected by filtration. Recrystallization from ethyl acetate provided the title product, m.p. 224°–225° (65 mg, 0.17 mmol, 14% yield).

EXAMPLE 22

6-Fluoro-1-(2-fluoroethyl)-1,4-dihydro-4-oxo-7-(6-[5,6,7,8-tetrahydro-1,6-naphthyridine])-quinoline-3-carboxylic acid A mixture of 5,6,7,8-tetrahydro-1,6-naphthyridine (300 mg, 2.24 mmol) and 6,7-difluoro-1-(2-fluoroethyl)-1,4-dihydro-4-oxo-quinoline-3-carboxylic acid (325 mg, 1.2 mmol) in pyridine (3 ml) was heated to 90° for 18 hours. The reaction mixture was filtered, and the precipitate triturated twice with refluxing ethyl acetate, then with refluxing isopropyl alcohol. The resulting solid was recrystallized from dimethylformamide to provide the title product as a solid, m.p. 261°–262° (50 mg, 0.13 mmol, 11% yield).

PREPARATION OF STARTING MATERIALS

EXAMPLE 4

6,7-Difluoro-1-(2-fluoroethyl)-1,4-dihydro-4-oxo-quinoline-3-carboxylic acid ethyl ester 1. 6,7-Difluoro-1,4-dihydro-4-oxo-quinoline-3-carboxylic acid ethyl ester (10.0 g, 39.5 mmol), 1-bromo-2-fluoroethane (25.1 g, 197.5 mmol) and potassium carbonate (10.9 g, 79 mmol) were combined in dimethylformamide (200 ml) and heated to 90° for 20 hours. The reaction mixture was poured into cold water (1.5 l), and the copious precipitate was filtered. The precipitate was washed with cold water and recrystallized from ethyl acetate to provide the title product as light brown needles, m.p. 178°–180° (8.22 g, 27.5 mmol, 70% yield).

6,7-Difluoro-1-(2-fluoroethyl)-1,4-dihydro-4-oxo-quinoline-3-carboxylic acid 2. 6,7-Difluoro-1-(2-fluoroethyl)-1,4-dihydro-4-oxo-quinoline-3-carboxylic acid ethyl ester (7.74 g, 25.9 mmol) was mixed with aqueous 1N hydrochloric acid solution (300 ml), and heated to reflux for 2 hours. The reaction mixture was cooled, filtered, and the precipitate was washed with water and dried under vacuum to provide the title product as a white solid, m.p. 249°–251° (6.07 g, 22.4 mmol, 86% yield).

$^1$H NMR (DMSO-$d_6$): 9.05 (s, 1H), 8.35 (m, 2H), 5.03 (m, 1H), 4.93 (m, 2H), 4.75 (m, 1H).

EXAMPLE B 6,7-Difluoro-1,4-dihydro-1-methyl-4-oxo-quinoline-3-carboxylic acid ethyl ester 1. 6,7-Difluoro-1,4-dihydro-4-oxo-quinoline-3-carboxylic acid ethyl ester (10.0 g, 39.5 mmol), methyl iodide (56 g, 395 mmol) and potassium carbonate (10.9 g, 79 mmol) were combined in dimethylformamide and heated to 90° for 20 hours. The reaction mixture was cooled and poured into cold water (1.5 l). The precipitate was filtered, washed with cold water and recrystallized from ethyl acetate to yield the title product as white needles, m.p. 210°–212° (6.60 g, 24.7 mmol, 63% yield).

6,7-Difluoro-1,4-dihydro-1-methyl-4-oxo-quinoline-3-carboxylic acid 2. 6,7-Difluoro-1,4-dihydro-1-methyl-4-oxo-quinoline-3-carboxylic acid ethyl ester (7.24 g, 27.1 mmol) was mixed with 1N hydrochloric acid (300 ml) and heated to reflux for 2 hours. The reaction mixture was filtered, and the precipitate washed with water and dried under vacuum to provide the title product as a white solid, m.p. 284°–287° (5.78 g, 24.2 mmol, 89% yield).

$^1$H NMR (CF$_3$COOD): 9.42 (s, 1H), 8.5 (apparent t, J=7 Hz, 1H), 8.19 (dd, J=8, 13 Hz, 1H), 4.5 (s, 3H).

EXAMPLE C

2-Chloro-4,5-difluorobenzoyl chloride 1. 2-Chloro-4,5-difluorobenzoic acid (19.2 g, 0.1 mol) was mixed with thionyl chloride (50 ml) and heated to reflux for 3 hours. The reaction mixture was evaporated to dryness, and the residue dissolved in methylene chloride. Solvent was removed in vacuo, and the procedure repeated once with methylene chloride and once with benzene. The material (19 g, 0.09 mol, 90% yield) was used without further purification.

2-Chloro-4,5-difluoro-α-oxobenzenepropanoic acid ethyl ester

2. Malonic acid monoethyl ester (26 g, 199 mmol) was dissolved in tetrahydrofuran (500 ml) and cooled to −70°. After the addition of n-butyllithium (112.5 ml of a 1.6M solution in hexanes, 180 mmol), the reaction mixture was allowed to warm to −10°, and additional n-butyllithium was added (112.5 ml, as above). The resulting milky-white mixture was cooled to −70°, and treated with 2-chloro-4,5-difluorobenzoyl chloride (19 g, 90 mmol) in tetrahydrofuran (200 ml). After warming to room temperature, the reaction mixture was allowed to stir for an additional 2 hours, then poured into 2N hydrochloric acid (750 ml). The aqueous mixture was extracted with ethyl ether, and the combined organic layers were dried and concentrated to provide the title product as a light amber oil (20.6 g, 78.6 mmol, 87% yield), which was used without further purification.

2-(2-Chloro-4,5-difluorobenzoyl)-3-ethoxy-2-propenoic acid ethyl ester 3. 2-Chloro-4,5-difluoro-α-oxo-benzenepropanoic acid ethyl ester (20 g, 76 mmol), triethylorthoformate (17.0 g, 115 mmol) and acetic anhydride (19.5 g, 191 mmol) were combined and heated to reflux for 3 hours. Excess solvent was removed in vacuo to provide the crude title product, which was used without purification.

2-(2-Chloro-4,5-difluorobenzoyl)-3-(4-fluroanilino)-2-propenoic acid ethyl ester 4. 2-(2-Chloro-4,5-difluorobenzoyl)-3-ethoxy-2-propenoic acid ethyl ester (material from preceding preparation) was mixed with isopropyl alcohol (250 ml) and cooled to 0°. 4-Fluoroaniline (9.33 g, 84.0 mmol) was added, and the reaction mixture was allowed to warm to room temperature and stir for 18 hours. The precipitate was filtered and washed with isopropyl ether, yielding the title product (11.0 g, 28.7 mmol). Additional product (10.2 g, 26.6 mmol, 73% overall yield for two steps) was obtained from the filtrate, which was concentrated in vacuo and subjected to column chromatography (eluting with chloroform), providing material was was further purified by recrystallization from ether/hexanes.

$^1$H NMR (CDCl$_3$): 12.7 and 11.3 (bd, 1H), 8.6 and 8.5 (d, 1H), 7.2 (m, 6H), 4.0 (m, 2H), 1.1 and 0.9 (t, 3H).

6,7-Difluoro-1-(4-fluorophenyl)-1,4-dihydro-4-oxo-quinoline-3-carboxylic acid ethyl ester 5. 2-(2-Chloro-4,5-difluorobenzoyl)-3-(4-fluoroanilino)-2-propenoic acid ethyl ester (11.0 g, 28.7 mmol) was dissolved in dimethoxyethane (200 ml) and cooled to 0°. Sodium hydride (1.65 g of a 50% suspension in mineral oil, 34.5 mmol) was added portionwise, and the mixture was heated to reflux for 3 hours. The reaction mixture was then poured into water (2 l) and the title product was collected by filtration (8.96 g, 25.8 mmol, 90% yield).

$^1$H NMR (DMSO-d$_6$): 8.5 (s, 1H), 8.1 (dd, J=6, 7 Hz, 1H), 7.7 (m, 2H), 7.5 (m, 2H) 7.0 (dd, J=5, 8 Hz, 1H), 4.2 (q, J=5 Hz, 2H), 1.3 (t, J=5 Hz, 3H).

6,7-Difluoro-1-(4-fluorophenyl)-1,4-dihydro-4-oxo-quinoline-3-carboxylic acid 6. 6,7-Difluoro-1-(4-flurophenyl)-1,4-dihydro-4-oxo-quinoline-3-carboxylic acid ethyl ester (14.5 g, 42 mmol) was mixed with acetic acid (300 ml), treated with 1N hydrochloric acid (100 ml) and heated to 100° for 4 hours. The reaction mixture was cooled and filtered, and the precipitate washed with water and ethyl ether to provide the title product as a solid, m.p. 252°–256° (11.5 g, 36.0 mmol, 86% yield).

$^1$H NMR (DMSO-d$_6$): 8.8 (s, 1H), 8.3 (dd, J=6, 7 Hz, 1H), 7.8 (m, 2H), 7.6 (m, 2H), 7.2 (dd, J=5, 8 Hz, 1H).

EXAMPLE D

4-N-Phthalimido-2-butanone

1. Phthalimide (90 g, 0.61 mol) and Triton B (15.3 ml of a 40% solution in methanol, 0.61 mol) were suspended in ethyl acetate (350 ml) and treated with methyl vinyl ketone (51 ml, 0.61 mol). Additional ethyl acetate (75 ml) was added to facilitate stirring of the heterogeneous mixture. The reaction mixture was heated to reflux for 50 minutes and then concentrated in vacuo, providing a light brown solid; this was recrystallized from ethanol to give the title product as an off-white solid, m.p. 109°–111° (76.48 g, 0.35 mol, 58% yield)

$^1$H NMR (CDCl$_3$): 7.8 (m, 2H), 7.7 (m, 2H), 3.94 (t, J=7 Hz, 2H), 2.86 (t, J=7 Hz, 2H), 2.18 (s, 3H).

1-Bromo-4-N-phthalimido-2-butanone 2. 4-N-phthalimido-2-butanone (70.0 g, 0.322 mol) was dissolved in methylene chloride (525 ml) and methanol (425 ml). A solution of bromine (16.5 ml, 0.322 mol) in methanol (100 ml) was added dropwise over a 2 hour period. The reaction mixture was allowed to stir overnight, and was then treated with additional bromine (4 ml, 0.078 mol); after 1 hour, no starting material was visible by TLC. The reaction mixture was concentrated in vacuo to leave a yellow solid, which was triturated with ether and dried under nitrogen to give the product as a white solid, m.p. 88°–90° C. (54.84 g, 0.185 mol, 58% yield).

$^1$NMR (CDCl$_3$): 7.82 (m, 2H), 7.72 (m, 2H), 4.01 (t, J=8 Hz, 2H), 3.93 (s, 2H), 3.12 (t, J=8 Hz, 2H).

2-Amino-4-[(2-N-phthalimido)ethyl]thiazole hydrochloride 3. 1-Bromo-4-N-phthalimido-2-butanone (50.0 g, 0.169 mol) and thiourea (25.71 g, 0.338 mol) were mixed with n-propanol (1000 ml) and concentrated hydrochloric acid (100 ml), and the reaction mixture was heated to reflux for 1.5 hour. After cooling, the precipitate was filtered and washed with n-propanol and ether. After air drying, the title product was obtained as a fluffy white solid (37.51 g, 0.121 mol, 72% yield), m.p. 230°–240° (decomp.).

$^1$H NMR (DMSO-d$_6$): 9.08 (bs, 2H), 7.84 (m, 4H), 6.53 (s, 1H), 3.84 (t, J=6 Hz, 2H), 2.83 (t, J=6 Hz, 2H).

2-Amino-4-[(2-N-phthalimido)ethyl]thiazole 4. 2-Amino-4-[(2-N-phthalimido)ethyl]thiazole hydrochloride (31.40 g, 0.101 mmol) was mixed with water (300 ml), heated to 80° and filtered. The filtrate was brought to a pH of 13 with saturated aqueous potassium carbonate solution, and the precipitated solid was filtered, washed with ether and air dried to leave a light brown solid (26.34 g, 96.4 mmol, 95% yield), m.p. 190°–194°.

$^1$H NMR (CDCl$_3$/CD$_3$OD): 7.75 (m, 2H), 7.66 (m, 2H), 6.07 (s, 1H), 3.90 (t, J=7 Hz, 2H), 2.84 (t, J=7 Hz, 2H).

2-Amino-4-(2-aminoethyl)thiazole 5. 2-Amino-4-[(2-N-phthalimido)ethyl]thiazole (4.00 g, 14.6 mmol) was added to a solution of hydrazine in methanol (200 ml, 0.2M), and the reaction mixture was heated for 0.5 hour until it became homogeneous. The reaction mixture was then stirred at room temperature for another 2 hours. Concentration in vacuo provided a white solid, which was purified by column chromatography (eluant: 89:10:1 chloroform:methanol:concentrated ammonium hydroxide). The title product was obtained as a white solid, m.p. 69°–71° (1.82 g, 12.7 mmol, 87% yield).

$^1$H NMR (DMSO-d$_6$): 6.79 (s, 2H), 6.10 (s, 1H), 2.73 (t, J=6 Hz, 2H), 2.45 (t, J=6 Hz, 2H), 2.2 (vbs, H).

2-Amino-4,5,6,7-tetrahydrothiazolo[5,4-c]pyridine

6. A solution of 2-amino-4-(2-aminoethyl)thiazole (1.57 g, 11.0 mmol) in methanol (120 ml) was treated with acetic acid (0.15 ml, 2.6 mmol) and formaldehyde (0.89 ml of a 37% aqueous solution, 11 mmol). After ten minutes, the reaction mixture was concentrated in vacuo and subjected to column chromatography (eluant: 95:4:1 chloroform:methanol:concentrated ammonium hydroxide). The product was obtained as a white solid, m.p. 169°–173° (1.547 g, 10.0 mmol, 91% yield).

$^1$H NMR (DMSO-d$_6$): 6.64 (s, 2H), 3.59 (s, 2H), 2.87 (t, J=6 Hz, 2H), 2.33 (bt, 2H).

EXAMPLE E

5-Acetyl-2-amino-4,5,6,7-tetrahydrothiazolo[5,4-c]pyridine

1. N-Acetyl-3-bromo-4-piperidone hydrobromide (3.0 g, 9.9 mmol) was added slowly to a solution of thiourea (756 mg, 9.9 mmol) in dry ethanol (13.5 ml) at 60°. After completion of the addition, the reaction mixture was allowed to stir at 40° for 1 hour; the ethanol was then distilled off at atmospheric pressure, and the residue was heated to 160°–170° for 20 minutes. The reaction mixture was then cooled and dissolved in water, neutralized with saturated aqueous sodium bicarbonate, and extracted three times with chloroform. The combined organic layers were dried over sodium sulfate, filtered and concentrated to give an oil. Purification was effected by flash column chromatography (9:1 chloroform:methanol) to provide the title product as a solid (200 mg, 1.0 mmol, 10% yield).

$^1$H NMR (D$_2$O): 4.54 and 4.50 (bs, 2H), 3.8 (m, 2H), 2.64 and 2.56 (m, 2H), 1.20 and 1.15 (s, 3H).

2-Amino-4,5,6,7-tetrahydrothiazolo[5,4-c]pyridine 2. 5-Acetyl-2-amino-4,5,6,7-tetrahydrothiazolo-[5,4-c]pyridine (110 mg, 0.51 mmol) was dissolved in ethanol (1 ml) and treated with sodium hydroxide (15.4 mg, 0.38 mmol) in ethanol (1 ml). The solution was heated to 100° for 16 hours, then treated with additional sodium hydroxide (25.6 mg, 0.64 mmol) and heated to reflux for an additional 16 hours. Solid ammonium chloride was added, and the mixture was filtered and concentrated in vacuo. The residue was dissolved in chloroform, dried over sodium sulfate and solvent was removed, leaving the title product (67.4 mg, 0.43 mmol, 84% yield) as a yellow solid, which was used without further purification.

EXAMPLE F 2-(3-Pyridyl)amino-4-[(2-N-phthalimido)ethyl]thiazole 1. 1-Bromo-4-N-phthalimido-2-butanone (3.07 g, 10.3 mmol) and N-3-pyridyl thiourea (1.59 g, 10.3 mmol) were combined in acetone (100 ml) and heated to reflux for 26 hours. The precipitate was filtered, washed with acetone and dried, giving a green-yellow solid which was subjected to column chromatography (89:10:1 chloroform:methanol:concentrated aqueous ammonium hydroxide) to yield the title product (1.9 g, 5.2 mmol, 50% yield).

$^1$H NMR (DMSO-d$_6$): 8.6 (d, J=3 Hz, 1H), 8.0 (m, 2H), 7.8 (m, 4H), 7.1 (dd, J=8, 5 Hz, 1H), 6.6 (s, 1H), 3.87 (t, J=7 Hz, 2H), 2.9 (t, J=7 Hz, 2H).

2-(3-Pyridyl)amino-4-(2-aminoethyl)thiazole 2. 2-(3-Pyridyl)amino-4-[(2-N-phthalimido)ethyl]thiazole (1.88 g, 5.1 mmol) and hydrazine (16.4 mmol) were combined in methanol (55 ml) and allowed to stir at room temperature for 20 hours. The mixture was filtered, and the filtrate was concentrated to 1.61 g of an oil which was composed of the title product contaminated with a phthalimide-derived byproduct. The mixture was used in the next reaction without purification.

Partial $^1$H NMR (DMSO-d$_6$): 8.7 (d, J=2 Hz, 1H), 8.1 (m, 2H), 7.3 (dd, J=8, 5 Hz, 1H), 6.56 (s, 1H), 2.9 (t, J=7 Hz, 2H), 2.7 (t, J=7 Hz, 2H).

2-(3-Pyridyl)amino-4,5,6,7-tetrahydrothiazolo[5,4-c]-pyridine 3. 2-(3-Pyridyl)amino-4-(2-aminoethyl)thiazole (0.50 g, from preceding preparation) and acetic acid (0.19 ml, 3.3 mmol) were dissolved in methanol (23 ml) and treated with formaldehyde (0.19 ml of a 37% aqueous solution, 2.3 mmol). The reaction was allowed to stir at room temperatue for 18 hours, at which point additional formaldehyde (0.02 ml of a 37% aqueous solution, 0.25 mmol) was added. After an additional 2 hours, the reaction mixture was filtered; the filtrate was concentrated in vacuo, dissolved in aqueous base, and extracted with methylene chloride. The organic extracts were dried over sodium sulfate and concentrated to provide the title product (310 mg, 1.3 mmol, 57% yield).

$^1$H NMR (CDCl$_3$): 8.56 (d, J=2 Hz, 1H), 8.26 (m, 1H), 8.00 (m, 1H), 7.27 (dd, J=8, 5 Hz, 1H), 3.93 (m, 2H), 3.20 (t, J=6 Hz, 2H), 2.71 (m, 2H).

EXAMPLE G

2-Phenylamino-4-[(2-N-Phthalimido)ethyl]thiazole 1. 1-Bromo-4-N-phthalimido-2-butanone (4.00 g, 13.5 mmol) and phenylthiourea (4.19 g, 27.0 mmol) were mixed with n-propanol (80 ml) and concentrated hydrochloric acid (8 ml), and the reaction mixture was heated to reflux for 4 hours. After cooling, the precipitate was filtered and washed with n-propanol and ether. After air drying, a light orange solid (3.5 g) was obtained; this material was partitioned between ethyl acetate and saturated aqueous potassium carbonate. The organic layer was extracted twice with ethyl acetate, and the combined organic layers were dried over Na$_2$SO$_4$, filtered and concentrated in vacuo to leave an oily solid. This was crystallized from ether to give a yellow solid (1.72 g, 4.9 mmol, 36% yield).

$^1$H NMR (CDCl$_3$): 7.80 (m, 2H), 7.70 (m, 2H), 7.28 (m, 5H), 7.02 (m, 1H), 6.30 (s, 1H), 4.04 (t, J=7 Hz, 2H), 3.03 (t, J=7 Hz, 2H).

2-Phenylamino-4-(2-aminoethyl)thiazole 2. 2-Phenylamino-4-[(2-N-phthalimido)ethyl]thiazole (1.49 g, 4.26 mmol) was added to a solution of hydrazine in methanol (64 ml, 0.2M), and the reaction mixture was heated for 3 hours. Concentration in vacuo provided a solid, which was purified by column chromatography (eluant: 89:10:1 chloroform: methanol: concentrated ammonium hydroxide). The material obtained from the column was triturated with ether to provide the title product as a white solid (0.306 g, 1.40 mmol, 33% yield).

$^1$H NMR (CDCl$_3$): 7.32 (m, 5H), 7.04 (m, 1H), 6.26 (s, 1H), 3.07 (t, J=7 Hz, 2H), 2.77 (t, J=7 Hz, 2H).

2-Phenylamino-4,5,6,7-tetrahydrothiazolo[5,4-c]pyridine

3. A solution of 2-phenylamino-4-(2-aminoethyl)-thiazole (0.30 g, 1.37 mmol) in methanol (15 ml) was treated with acetic acid (0.02 ml, 0.35 mmol) and formaldehyde (0.11 ml of a 37% aqueous solution, 1.37 mmol). After 20 minutes, the reaction mixture was concentrated in vacuo and the residue dissolved in ethyl acetate. The organic layer was washed with saturated aqueous sodium bicarbonate, water, and saturated aqueous sodium chloride, dried over sodium sulfate, and concentrated in vacuo to provide a glassy solid (0.31 g, 1.34 mmol, 98% yield) which was used without further purification.

$^1$H NMR (DMSO-d$_6$): 10.0 (m, 1H), 7.60 (m, 2H), 7.28 (m, 2H), 6.92 (m, 1H), 3.74 and 3.65 (bs, 2H), 2.98 (m, 2H), 2.65 and 2.54 (bs, 2H).

EXAMPLE H

2-Dimethylamino-4-[(2-N-phthalimido)ethyl]thiazole 1. 1-Bromo-4-N-phthalimido-2-butanone (10.21 g, 34.46 mmol) and N,N-dimethylthiourea (3.59 g, 34.5 mmol) were combined in acetone (345 ml) and heated to reflux for 48 hours. The reaction mixture was filtered to provide the title product as a white solid (9.33 g, 31 mmol, 90% yield).

¹H NMR (DMSO-d₆): 7.83 (m, 4H), 6.70 (s, 1H), 3.88 (t, J=6 Hz, 2H), 3.21 (s, 6H), 2.92 (t, J=5 Hz, 2H).

2-Dimethylamino-4-(2-aminoethyl)thiazole 2. 2-Dimethylamino-4-[(2-N-phthalimido)ethyl]-thiazole (3.0 g, 9.96 mmol) was combined with hydrazine (30 mmol) in methanol (100 ml), and the reaction was allowed to stir for 16 hours at room temperature. A white precipitate was removed by filtration, and the title product was obtained upon concentration of the filtrate (2.9 g, contaminated with a phthalimide by-product as judged by 1H NMR). This material was used without further purification.

¹H NMR (DMSO-d₆): 8.03 (m, 2H), 7.77 (m, 2H), 6.38 (s, 1H), 3.00 (s, 6H), 2.91 (t, J=6 Hz, 2H), 2.64 (t, J=6 Hz, 2H).

2-Dimethylamino-4,5,6,7-tetrahydrothiazolo[5,4-c]-pyridine 3. 2-Dimethylamino-4-(2-aminoethyl)thiazole (1.7 g, see preceding preparation), formaldehyde (0.78 ml of a 37% solution in water, 9.6 mmol) and acetic acid (0.15 ml, 2.6 mmol) were combined in methanol (100 ml). After 2.5 hours at room temperature, the reaction mixture was treated with additional formaldehyde (0.15 ml, 1.8 mmol) and allowed to stir for an additional 16 hours. The reaction was then filtered, and the filtrate was concentrated in vacuo and purified by column chromatography (eluant: 89:10:1 of chloroform:methanol:concentrated ammonium hydroxide), providing the title product as a white solid (1.04 g, 5.7 mmol).

¹H NMR (CDCl₃): 3.84 (bs, 2H), 3.11 (t, J=8 Hz, 2H), 3.04 (s, 6H), 2.59 (m, 2H), 1.68 (bs, 1H).

EXAMPLE J

2-(Ethylamino-4-[(2-N-phthalimido)ethyl]thiazole 1. 1-Bromo-4-N-phthalimido-2-butanone (2.50 g, 8.44 mmol) and N-ethyl thiourea (0.88 g, 8.44 mmol) were combined in acetone (85 ml) and heated to reflux for 16 hours. The precipitate was filtered, washed with acetone and dried, giving a light yellow solid which was partitioned between ethyl acetate and saturated aqueous potassium carbonate. The organic layer was separated and dried over sodium sulfate. Removal of solvent in vacuo gave the title product as a yellow oil (2.03 g, 5.31 mmol, 63% yield) which was used without further purification.

¹H NMR (CDCl₃): 7.82 (m, 2H), 7.70 (m, 2H), 6.13 (s, 1H), 3.98 (t, J=7 Hz, 2H), 3.20 (m, 2H), 2.92 (t, J=7 Hz, 2H), 1.24 (t, J=7 Hz, 3H).

2-Ethylamino-4-(2-aminoethyl)thiazole 2. 2-Ethylamino-4-[(2-N-phthalimido)ethyl]thiazole (2.03 g, 5.31 mmol) and hydrazine (15.9 mmol) were combined in methanol (80 ml) and allowed to stir at 50° for 2 hours. The mixture was concentrated in vacuo, and the residue purified by column chromatography (eluant: 89:10:1 chloroform: methanol: concentrated aqueous ammonium hydroxide) to provide the title product as a yellow solid (0.63 g, 3.68 mmol, 69% yield).

¹H NMR (DMSO-d₆): 7.32 (bs, 1H), 6.10 (s, 1H), 3.12 (m, 2H), 2.72 (t, J=7 Hz, 2H), 2.45 (t, J=Hz, 2H), 1.10 (t, J=7 Hz, 3H).

2-Ethylamino-4,5,6,7-tetrahydrothiazolo[5,4-c]pyridine 3. 2-Ethylamino-4-(2-aminoethyl)thiazole (0.20 g, 1.17 mmol) and acetic acid (0.02 ml, 0.35 mmol) were dissolved in methanol (15 ml) and treated with formaldehyde (0.095 ml of a 37% aqueous solution, 1.17 mmol). The reaction was allowed to stir at room temperature for 15 minutes; it was then concentrated in vacuo and subjected to column chromatography (eluant: 89:10:1 chloroform: methanol: concentrated aqueous ammonium hydroxide). This provided the title product as a yellow solid (0.105 g, 0.57 mmol, 49% yield).

¹H NMR (DMSO-d₆): 7.22 (bt, J=5 Hz, 1H), 3.61 (s, 2H), 3.17 (m, 2H), 2.88 (t, J=6 Hz, 2H), 2.37 (m, 2H), 1.12 (t, J=7 Hz, 3H).

EXAMPLE K

5-Acetyl-2-guanidino-4,5,6,7-tetrahydrothiazolo[5,4-c]-pyridine

1. N-Acetyl-3-bromo-4-piperidone hydrobromide (12.09 g, 40 mmol) was added to a suspension of aminoiminomethylthiourea (4.735 g, 40 mmol) in ethanol (40 ml) at 70°. After completion of the addition, the reaction mixture was allowed to stir at 40° for 48 hours. Addition of sodium hydroxide (1.6 g, 40 mmol) was followed by stirring at 40° for an additional 72 hours. Removal of solvent gave a crude oil which was subjected to column chromatography (eluant: 89:10:1 of chloroform:methanol:concentrated ammonium hydroxide) to provide the title product (822 mg, 3.4 mmol, 9% yield).

¹H NMR (DMSO-d₆): 6.84 (bs, 4H), 4.50 and 4.46 (bs, 2H), 3.72 (m, 2H), 2.63 and 2.51 (bs, 2H), 2.11 and 2.06 (s, 3H).

2-Guanidino-4,5,6,7-tetrahydrothiazolo[5,4-c]pyridine 2. 5-Acetyl-2-guanidino-4,5,6,7-tetrahydrothiazolo[5,4-c]pyridine (232.4 mg, 0.971 mmol) was mixed with ethanol (7 ml) and treated with an aqueous solution of sodium hydroxide (1.98 ml of a 1.46M solution, 2.9 mmol). The reaction mixture was heated to 81° for 72 hours, then concentrated in vacuo; the residue was purified by column chromatography (eluant: 89:10:1 of chloroform:methanol:concentrated ammonium hydroxide) to provide the title product as an oil (129.9 mg, 0.66 mmol, 68% yield).

¹H NMR (DMSO-d₆): 6.75 (bs, 5H), 3.64 (bs, 2H), 2.93 (bs, 2H), 2.43 (bs, 2H).

EXAMPLE L

5-Acetyl-2-methyl-4,5,6,7-tetrahydrothiazolo[5,4-c]-pyridine

1. N-Acetyl-3-bromo-4-piperidone hydrobromide (5.0 g, 16.6 mmol) in acetone (160 ml) was heated to 60° and treated with triethylamine (2.31 ml, 33.1 mmol) and thioacetamide (1.24 g, 16.6 mmol). The reaction mixture was heated to reflux for 24 hours, then cooled and filtered, to provide a yellow solid which was purified by column chromatography (eluant:89:10:1 chloroform: methanol: concentrated aqueous ammonium hydroxide). The title product was obtained as a yellow oil (995 mg, 5.1 mmol, 31% yield).

¹H NMR (DMSO-d₆): 4.68 and 4.64 (bs, 2H), 3.74 (m, 2H), 2.82 and 2.69 (m, 2H), 2.13 and 2.09 (s, 3H).

2.Methyl-4,5,6,7-tetrahydrothiazolo[5,4-c]pyridine 2. 5-Acetyl-2-methyl-4,5,6,7-tetrahydrothiazolo[5,4-c]pyridine (990.4 mg, 5.05 mmol) was dissolved in ethanol (23 ml) and treated with sodium hydroxide (0.12 g, 3 mmol) in water (3.3 ml). The solution was heated to 50° for 40 hours, treated with additional sodium hydroxide (1.01 g, 25 mmol), and heated to reflux for an additional 32 hours. The ethanol was removed in vacuo, and the aqueous residue was extracted three times with methylene chloride. Adsorption of the aqueous layer onto potassium sulfate was followed by washing of the salts with methanol. The combined organic layers were concentrated in vacuo, and the resulting yellow oil was subjected to column chromatography (eluant: 89:10:1 chloroform: methanol: concentrated aqueous ammonium hydroxide) to provide the title product as a yellowish solid (311 mg, 2.0 mmol, 40% yield).

$^1$H NMR (DMSO-$d_6$): 3.83 (s, 2H), 2.97 (t, J=6 Hz, 2H), 2.60 (m, 5H).

EXAMPLE M 4,5,6,7-Tetrahydrothiazolo[5,4-c]pyridin-2(1H)-one

Ammonium thiocyanate (5.54 g, 72.8 mmol) was mixed with water (450 ml) and heated to 80°. A solution of N-acetyl-3-bromo-4-piperidone hydrobromide (20.0 g, 66.2 mmol) in water (200 ml) was added dropwise over 3 hours. The reaction was then allowed to stir at 80° for sixteen hours. The reaction solution (containing the crude N-acetyl-3-thiocyanato-4-piperidone) was treated with concentrated hydrochloric acid (6 ml of a 12M solution, 93 mmol) and heated to reflux for 2 hours. The reaction mixture was then freeze-dried, and the residue dissolved in methanol and filtered. The precipitate was purified by column chromatography (eluant: 89:10:1 chloroform:methanol: concentrated ammonium hydroxide) to provide the title product as a white solid, m.p. 208° (decomp.) (0.60 g, 3.8 mmol, 6% yield).

$^1$H NMR (DMSO-$d_6$): 3.40 (m, 2H), 3.30 (vbs, 1H), 2.89 (t, J=6 Hz, 2H), 2.20 (m, 2H).

EXAMPLE N

2-[(Dimethylamino)methylene]-1-triphenylmethyl-4-piperidone 1. 1-Triphenylmethyl-4-piperidone (0.239 g, 0.70 mmol) was added to methoxybis(dimethylamino)methane (1.75 ml) and the reaction mixture was stirred at 50° for sixteen hours. Volatiles were then removed in vacuo to provide a yellow solid, which was triturated with ether, and air dried to give the title product as a light yellow solid (0.179 g, 0.45 mmol, 64% yield).

$^1$H NMR (CDCl$_3$): 7.56–7.15 (m, 16H), 3.33 (bs, 2H), 2.91 (s, 6H), 2.6–2.5 (m, 4H).

2-Amino-5,6,7,8-tetrahydro-6-triphenylmethyl-pyrido[4,3-d]-pyrimidine 2. 2-[(Dimethylamino)methylene]-1-triphenylmethyl-4-piperidone (0.172 g, 0.434 mmol) was dissolved in ethyl acetate (4 ml) and treated with guanidine carbonate (47 mg, 0.260 mmol). The reaction mixture was heated to reflux for sixteen hours, and then concentrated in vacuo. Purification of the residue via flash column chromatography (eluant: 3:1 ethyl acetate: hexanes) yielded the title product as a yellow oil (83 mg, 0.21 mmol, 48% yield).

$^1$H NMR (DMSO-$d_6$): 7.90 (s, 1H), 7.46 (bd, J=8 Hz, 6H), 7.35 (t, J=7 Hz, 6H), 7.22 (t, J=7 Hz, 3H), 6.36 (bs, 2H), 3.15 (bs, 2H), 2.83, (bs, 2H), 2.45 (bs, 2H).

2-Amino-5,6,7,8-tetrahydropyrido[4,3-d]pyrimidine 3. 2-Amino-5,6,7,8-tetrahydro-6-triphenylmethyl-pyrido-[4,3-d]pyrimidine (80 mg, 0.20 mmol) was mixed with water (0.5 ml) and acetic acid (0.5 ml) and heated on a steam bath for 5 minutes. Addition of acetone provided a homogeneous mixture. Removal of solvents gave an oil, which was purified by flash column chromatography (eluant: 89:10:1 chloroform:methanol:concentrated ammonium hydroxide) to provide the title product (24.3 mg, 0.16 mmol, 80% yield).

$^1$H NMR (CD$_3$OD): 7.98 (s, 1H), 3.80 (s, 2H), 3.12 (t, J=6 Hz, 2H), 2.71 (t, J=6 Hz, 2H).

EXAMPLE O 1,6-Naphthyridine

1. Glycerol (138.15 g, 1.5 mol) was added dropwise to an ice-cold mixture of "sulfo-mix" (a mixture of nitrobenzene and fuming sulfuric acid, see: Utermohlen, W. P., *J. Org. Chem*, 1943 8, 544). Addition of 4-aminopyridine (56.46 g, 0.6 mol) was followed by a rapid dropwise addition of water (225 ml), which caused a rise in temperature to 80°; the reaction mixture was allowed to stir until it became homogeneous, and was subsequently heated to 135° for 48 hours. It was then allowed to cool, poured into 1 l ice water, and the pH was adjusted to 13 by the addition of sodium hydroxide pellets. The resulting thick precipitate was removed by filtration, and the filtrate was extracted with methylene chloride (2×2 l). The combined organic extracts were dried over sodium sulfate, filtered, and concentrated to yield a crude product, which was purified by column chromatography (98:2 methylene chloride:methanol). The title product was obtained as an amber oil which crystallized upon standing (13.7 g, 0.11 mol, 18% yield).

6-Benzyl-5,6,7,8-tetrahydro-1,6-naphthyridine 2. 1,6-Naphthyridine (13.7 g, 105 mmol) and benzyl bromide (36.05 g, 210 mmol) were combined in acetonitrile (200 ml) and heated to reflux until no 1,6-naphthyridine was visible by thin layer chromatography. After removal of the solvent in vacuo, the residue was washed several times with ether and dissolved in methanol (700 ml). Water (250 ml) was added, and the solution cooled to 0°; portionwise addition of sodium borohydride (20.8 g, 550 mmol) brought about vigorous gas evolution and a slight rise in temperature. The reaction mixture was allowed to warm to room temperature and stir for 18 hours. The solvent was then removed in vacuo and the residue partitioned between water (750 ml) and methylene chloride (300 ml). The aqueous layer was extracted with additional methylene chloride (2×300 ml) and the combined organic extracts were washed once with water and once with saturated aqueous sodium chloride. Removal of solvent provided a dark amber foam, which was purified by column chromatography (99:1 methylene chloride:methanol) to yield the title product (12.1 g, 54 mmol, 51% yield).

5,6,7,8-Tetrahydro-1,6-naphthyridine 3. 6-Benzyl-5,6,7,8-tetrahydro-1,6-naphthyridine (5.0 g, 22.3 mmol) was dissolved in acetic acid (150 ml) and treated with 10% palladium on carbon (2.5 g). The reaction mixture was subjected to 40 psig hydrogen at 55° on a Parr hydrogenation apparatus for 18 hours; the mixture was then filtered through Super-Cel. The filtrate was evaporated to an amber oil, which was dissolved in 6N sodium hydroxide solution and extracted with toluene (2×50 ml) and methylene chloride (2×50 ml). The combined organic extracts were dried over magnesium sulfate, and concentrated in vacuo to provide the title product as a light amber oil (2.8 g, 21 mmol, 94% yield).

We claim:

1. A compound of the formula:

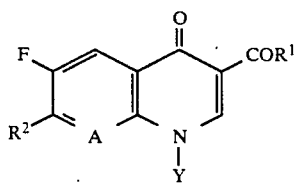

wherein

Y, when taken independently, is $(C_1-C_3)$alkyl, $(C_1-C_3)$hydroxyalkyl, vinyl, $(C_1-C_3)$haloalkyl wherein halo is fluoro or chloro, cyclopropyl, o,p-difluoro-phenyl, or p-fluorophenyl;

A, when taken independently, is C-H, C-F, C-Cl, C-OCH$_3$,

R$^1$ is hydroxy, $(C_1-C_6)$alkoxy, amino, $(C_1-C_6)$alkylamino, or OM wherein M is a pharmaceutically acceptable cation; and R$^2$ is

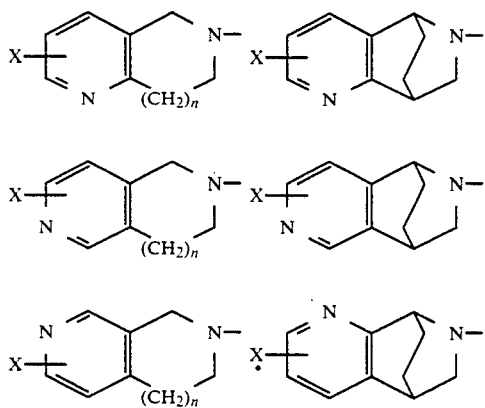

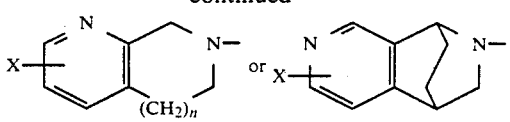

wherein X is hydrogen, or one or two of CH$_2$NHR$^4$, HNR$^4$ or $(C_1-C_6)$alkylsulfonyl wherein R$^4$ is hydrogen or $(C_1-C_6)$ alkyl wherein is 0 or 1.

2. A compound according to claim 1 wherein R$^1$ is hydroxy.

3. A compound according to claim 2 wherein A is C-H.

4. A compound according to claim 3 wherein R$^2$ is 6-[5,6,7,8-tetrahydro-1,6-naphthyridine].

5. A compound according to claim 1 wherein said compound is
1-ethyl-6-fluoro-1,4-dihydro-oxo-7-[6-(5,6,7,8-tetrahydro-1,6-naphthyridine)]-quinoline-3-carboxylic acid,
1-cyclopropyl-6-fluoro-1,4-dihydro-4-oxo-7-[6-(5,6,7,8-tetrahydro-1,6-naphthyridine)]1,8-naphthyridine-3-carboxylic acid,
1-vinyl-6-fluoro-1,4-dihydro-4-oxo-7-[6-(5,6,7,8-tetrahydro-1,6-naphthyridine)]-quinoline-3-carboxylic acid,
1-cyclopropyl-6-fluoro-1,4-dihydro-4-oxo-7-[6-(5,6,7,8-tetrahydro-1,6-naphthyridine)]-quinoline-3-carboxylic acid,
6-fluoro-1-(4-fluorophenyl)-1,4-dihydro-4-oxo-7-[6,(5,6,7,8-tetrahydro-1,6-naphthyridine)]-quinoline-3-carboxylic acid, or
6-fluoro-1-(2-fluoroethyl)-1,4-dihydro-4-oxo-7-[6-(5,6,7,8-tetrahydro-1,6-naphthyridine)]-quinoline-3-carboxylic acid, or a pharmaceutically acceptable acid addition or base salt thereof.

6. An antibacterial composition comprising an antibacterially effective amount of a compound according to claim 1 and a pharmaceutically acceptable carrier.

7. A method for the treatment of bacterial diseases which comprises administering to a subject affected by a bacterial disease an antibacterially effective amount of a compound according to claim 1.

* * * * *